(12) United States Patent
Cao et al.

(10) Patent No.: US 12,144,666 B2
(45) Date of Patent: *Nov. 19, 2024

(54) MULTI-SOURCE CONE BEAM COMPUTED TOMOGRAPHY

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 260 days.

This patent is subject to a terminal disclaimer.

(21) Appl. No.: 17/863,728

(22) Filed: Jul. 13, 2022

(65) Prior Publication Data

US 2022/0346733 A1 Nov. 3, 2022

Related U.S. Application Data

(63) Continuation of application No. PCT/CN2020/076912, filed on Feb. 27, 2020.

(51) Int. Cl.
*A61B 6/03* (2006.01)
*A61B 6/00* (2024.01)
(Continued)

(52) U.S. Cl.
CPC .......... *A61B 6/4028* (2013.01); *A61B 6/032* (2013.01); *A61B 6/4007* (2013.01); *A61B 6/4014* (2013.01); *A61B 6/405* (2013.01); *A61B 6/4085* (2013.01); *A61B 6/4266* (2013.01); *A61B 6/5241* (2013.01); *G01N 23/046* (2013.01); *G01T 1/2985* (2013.01); *G01V 5/226* (2024.01)

(58) Field of Classification Search
CPC ..... A61B 6/4208; A61B 6/032; A61B 6/4007; A61B 6/4014; A61B 6/405; A61B 6/4085; A61B 6/4266; A61B 6/5241; G01N 23/046; G01T 1/2985; G01V 5/226
See application file for complete search history.

(56) References Cited

U.S. PATENT DOCUMENTS 7,933,378 B2 * 4/2011 Proksa ................ A61B 6/4014
378/9
8,693,638 B2 4/2014 Dafni
(Continued)

FOREIGN PATENT DOCUMENTS

CN 1476312 A 2/2004
CN 104142505 A 11/2014
(Continued)

*Primary Examiner* — Mark R Gaworecki
(74) *Attorney, Agent, or Firm* — IPro, PLLC

(57) ABSTRACT

Disclosed herein is an apparatus comprising: a first radiation source configured to produce a first divergent radiation beam toward an object; a second radiation source configured to produce a second divergent radiation beam toward the object; and an image sensor; wherein the object is configured to rotate with respect to the image sensor, the first radiation source, and the second radiation source, and wherein relative positions among the image sensor, the first radiation source, and the second radiation source are fixed.

39 Claims, 27 Drawing Sheets

(51) Int. Cl.
*A61B 6/40* (2024.01)
*A61B 6/42* (2024.01)
*G01N 23/046* (2018.01)
*G01T 1/29* (2006.01)
*G01V 5/22* (2024.01)
*G01V 5/226* (2024.01)

(56) References Cited

U.S. PATENT DOCUMENTS

| | | | |
|---|---|---|---|
| 11,921,056 B2 * | 3/2024 | Cao | A61B 6/5241 |
| 2019/0239788 A1 | 8/2019 | Rudmann et al. | |

FOREIGN PATENT DOCUMENTS

| | | |
|---|---|---|
| CN | 110248604 A | 9/2019 |
| TW | 200643400 A | 12/2006 |
| WO | 2020019285 A1 | 1/2020 |

* cited by examiner

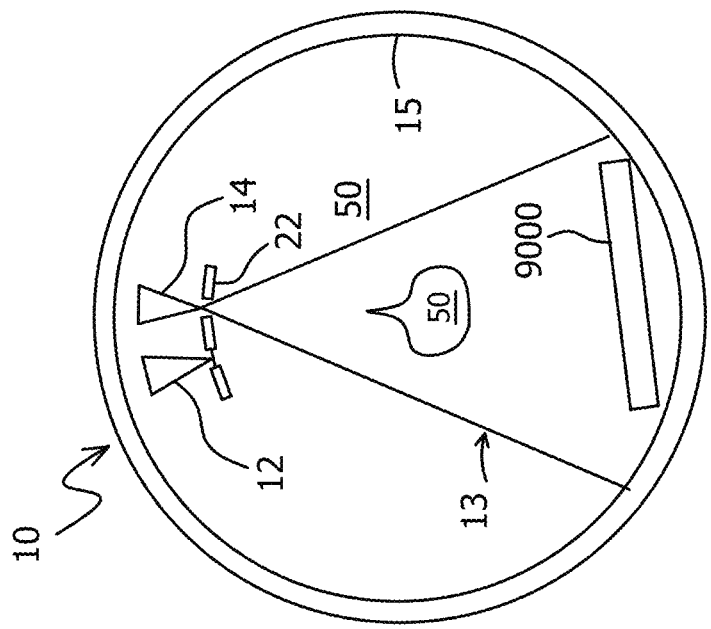
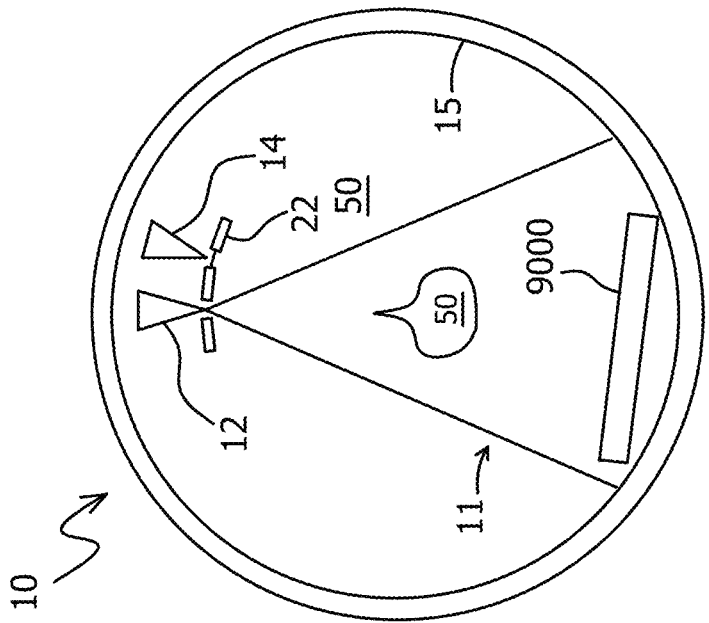
FIG. 1A
FIG. 1B

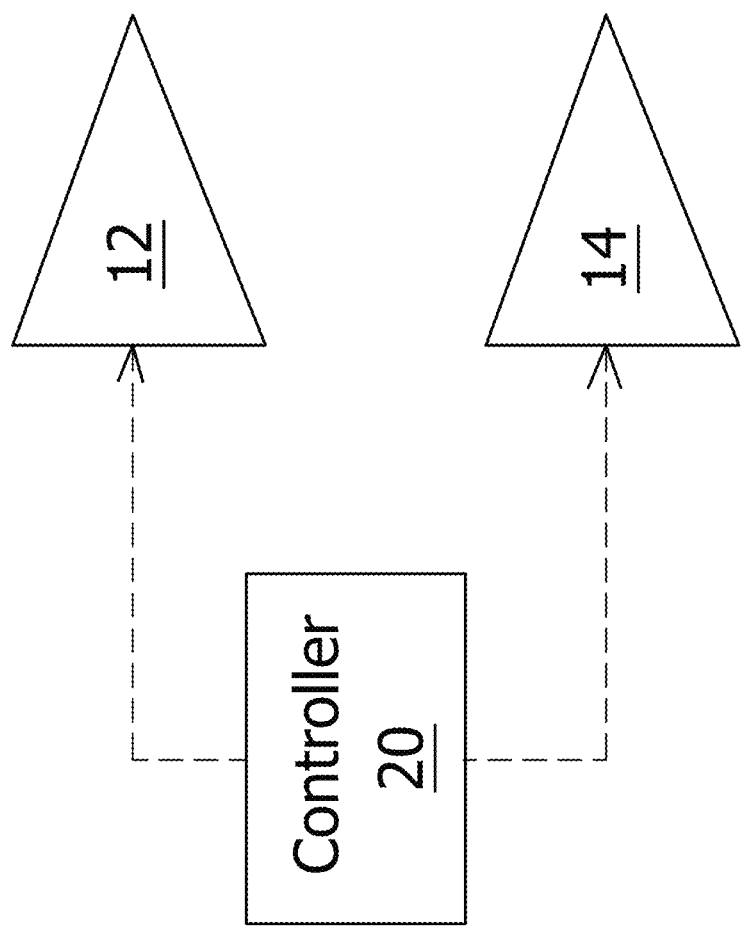

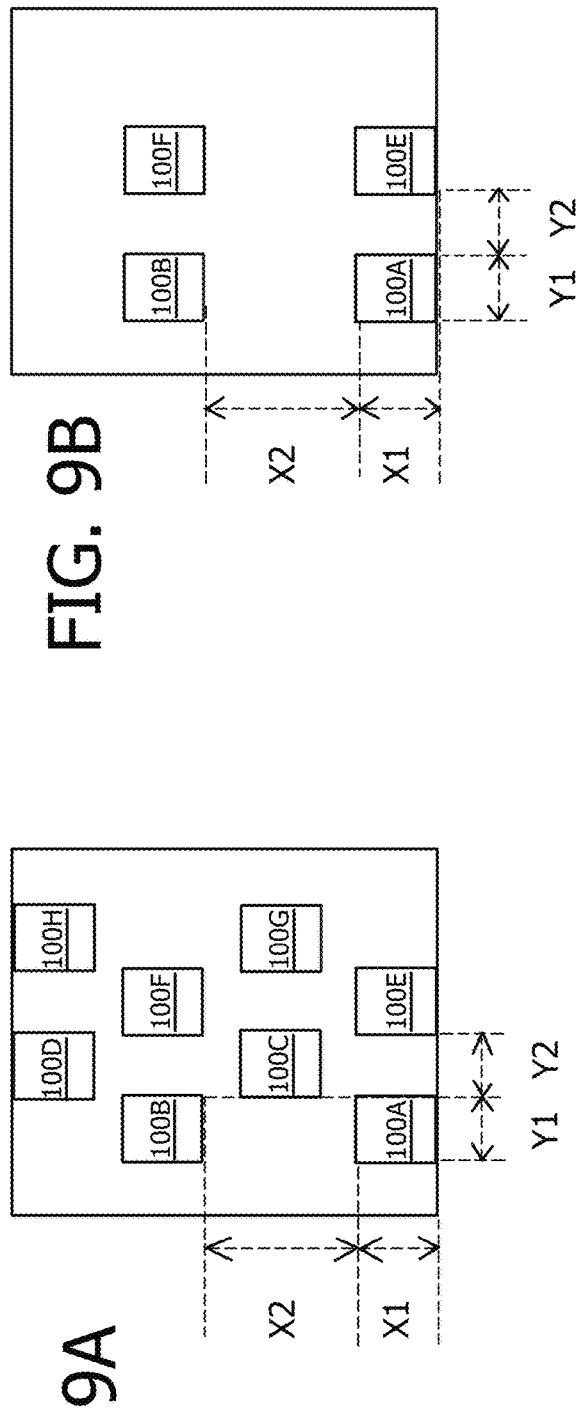
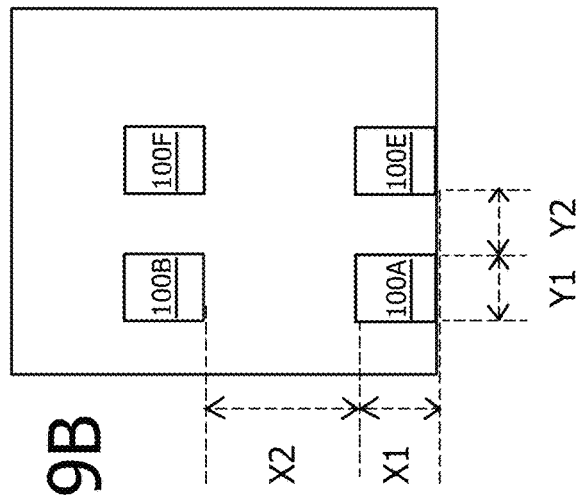
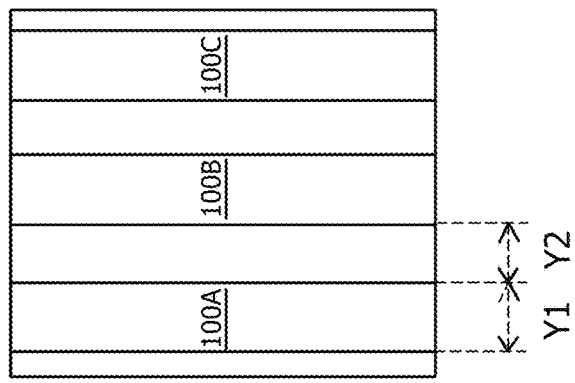
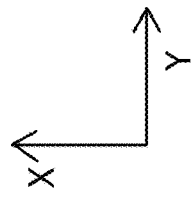
FIG. 9A
FIG. 9B
FIG. 9C

```
2200 ──▶ [2210: positioning components of the apparatus 10 and the object 50.] ──▶ [2220: directing divergent radiation beams toward the object 50.] ──▶ [2230: capturing portion images of portions of the object 50.] ──▶ [2240: forming stitched images.]
```

FIG. 22

MULTI-SOURCE CONE BEAM COMPUTED TOMOGRAPHY

TECHNICAL FIELD

The disclosure herein relates to cone beam computed tomography (CBCT).

BACKGROUND

Cone beam computed tomography (CBCT) is a type of computed tomography (CT). Compared to conventional CT, CBCT uses a divergent radiation beam to illuminate an object being imaged and may provide better image accuracy, shorter scan time, and lower doses. CBCT may be useful in various applications such as implantology, orthodontics, orthopedics, and interventional radiology.

SUMMARY

Disclosed herein is an apparatus comprising: a first radiation source configured to produce a first divergent radiation beam toward an object; a second radiation source configured to produce a second divergent radiation beam toward the object; and an image sensor; wherein the object is configured to rotate with respect to the image sensor, the first radiation source, and the second radiation source, and wherein relative positions among the image sensor, the first radiation source, and the second radiation source are fixed.

In an aspect, the image sensor, the first radiation source, and the second radiation source are stationary.

In an aspect, the first and second divergent radiation beams are X-rays with photon energy being less than 5 KeV.

In an aspect, said rotation of the object is around a rotation axis perpendicular to an apparatus plane which intersects the image sensor, the first radiation source, and the second radiation source.

In an aspect, the apparatus further comprises a platform, wherein the object is physically fixed to the platform, and wherein the platform is configured to rotate with respect to the image sensor, the first radiation source, and the second radiation source.

In an aspect, the apparatus further comprises a controller configured to activate and deactivate the first radiation source independently from the second radiation source, and configured to activate and deactivate the second radiation source independently from the first radiation source.

In an aspect, the apparatus further comprises a shutter configured to controllably block the first divergent radiation beam from reaching the object, and to controllably block the second divergent radiation beam from reaching the object.

In an aspect, the image sensor is configured to capture an image of a portion of the object with the first divergent radiation beam or with the second divergent radiation beam.

In an aspect, the image sensor comprises a collimator with a plurality of radiation transmitting zones and a radiation blocking zone; wherein the radiation blocking zone is configured to block radiation that would otherwise incident on a dead zone of the image sensor, and the radiation transmitting zones are configured to transmit at least a portion of radiation that would incident on active areas of the image sensor.

In an aspect, the apparatus further comprises a mask with a plurality of radiation transmitting zones and a radiation blocking zone; wherein the radiation blocking zone is configured to block a portion of the first divergent radiation beam that would otherwise incident on a dead zone of the image sensor through the object, and the radiation transmitting zones are configured to transmit at least a portion of the first divergent radiation beam that would incident on active areas of the image sensor.

In an aspect, the image sensor comprises: a plurality of radiation detectors spaced apart from one another; wherein the image sensor is configured to capture, by using the radiation detectors and with the first divergent radiation beam, an image of a first portion of the object, and is configured to capture, by using the radiation detectors and with the second divergent radiation beam, an image of a second portion of the object; wherein the image sensor is configured to form an image of the object by stitching the image of the first portion and the image of the second portion.

In an aspect, the radiation detectors respectively comprise radiation receiving surfaces not all parallel to each other.

In an aspect, for each radiation detector of the radiation detectors, any straight line going through said radiation detector and either the first radiation source or the second radiation source is essentially perpendicular to a radiation receiving surface of said radiation detector.

In an aspect, the first radiation source is at a first radiating position relative to the object when the image sensor captures the image of the first portion of the object and the second radiation source is at a second radiating position relative to the object when the image sensor captures the image of the second portion of the object; wherein the first radiating position and the second radiating position are the same.

In an aspect, at least some of the plurality of radiation detectors are arranged in staggered rows.

In an aspect, radiation detectors in a same row are uniform in size; wherein a distance between two neighboring radiation detectors in a same row is greater than a width of one radiation detector in the same row in an extending direction of the row and is less than twice that width.

In an aspect, at least some of the plurality of radiation detectors are rectangular in shape.

In an aspect, at least some of the plurality of radiation detectors are hexagonal in shape.

In an aspect, at least one of the plurality of radiation detectors comprises a radiation absorption layer and an electronics layer; wherein the radiation absorption layer comprises an electrode; wherein the electronics layer comprises an electronic system; wherein the electronic system comprises: a first voltage comparator configured to compare a voltage of the electrode to a first threshold, a second voltage comparator configured to compare the voltage to a second threshold, a counter configured to register a number of particles of radiation reaching the radiation absorption layer, and a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

In an aspect, the electronic system further comprises an integrator electrically connected to the electrode, wherein the integrator is configured to collect charge carriers from the electrode.

In an aspect, the controller is configured to activate the second voltage comparator at a beginning or expiration of the time delay.

In an aspect, the electronic system further comprises a voltmeter, wherein the controller is configured to cause the voltmeter to measure the voltage upon expiration of the time delay.

In an aspect, the controller is configured to determine an energy of particles of radiation based on a value of the voltage measured upon expiration of the time delay.

In an aspect, the controller is configured to connect the electrode to an electrical ground.

In an aspect, a rate of change of the voltage is substantially zero at expiration of the time delay.

In an aspect, a rate of change of the voltage is substantially non-zero at expiration of the time delay.

Disclosed herein is a method, comprising: for i=1, . . . ,M, and j=1, . . . ,N, positioning a radiation source (j) and a same object such that the radiation source (j) is at a same relative radiating position (i) with respect to the object; directing a divergent radiation beam (i,j) from the radiation source (j) toward the object while the radiation source (j) is at the relative radiating position (i) with respect to the object; capturing a portion image (i,j) of a portion of the object using a same image sensor with the divergent radiation beam (i,j); and for i=1, . . . ,M, forming a stitched image (i) of the object by stitching the portion images (i,j), j=1, . . . ,N, wherein said positioning comprises rotating the object with respect to the image sensor and the radiation sources (j), j=1, . . . ,N, wherein relative positions among the image sensor and the radiation sources (j), j=1, . . . ,N are fixed, and wherein M and N are integers greater than 1.

In an aspect, the image sensor and the radiation sources (j), j=1, . . . ,N are stationary.

In an aspect, the divergent radiation beam (i,j) is X-ray with photon energy being less than 5 KeV.

In an aspect, said rotation of the object is around a rotation axis perpendicular to an apparatus plane which intersects the image sensor and the radiation sources (j), j=1, . . . ,N.

In an aspect, the object is physically fixed to a platform, and wherein said rotating the object comprises rotating the platform.

In an aspect, each radiation source of the radiation sources (j), j=1, . . . ,N is deactivated while said radiation source is not at a relative radiating position of the relative radiating positions (i), i=1, . . . ,M.

In an aspect, radiation produced by each radiation source of the radiation sources (j), j=1, . . . ,N is blocked while said radiation source is not at a relative radiating position of the relative radiating positions (i), i=1, . . . ,M.

In an aspect, a portion of each divergent radiation beam of the divergent radiation beams (i,j), i=1, . . . ,M, and j=1, . . . ,N that would otherwise incident on a dead zone of the image sensor through the object is blocked.

In an aspect, the image sensor comprises a plurality of radiation detectors spaced apart from one another, and wherein said capturing the portion image (i,j) of a portion of the object comprises receiving a portion of the divergent radiation beam (i,j) that has transmitted through the object, with the radiation detectors.

In an aspect, the radiation detectors respectively comprise radiation receiving surfaces not all parallel to each other.

In an aspect, for each radiation detector of the radiation detectors, any straight line going through said radiation detector and any radiation source of the radiation sources (j), j=1, . . . ,N is essentially perpendicular to a radiation receiving surface of said radiation detector.

In an aspect, for i=1, . . . ,M, the portion images (i,j), j=1, . . . ,N have spatial overlaps.

In an aspect, the method further comprises forming a 3D (three dimensional) image of an object surface of the object based on the stitched images (i), i=1, . . . ,M.

In an aspect, the method further comprises forming a mold based on and conforming to the 3D image of the object surface.

BRIEF DESCRIPTION OF FIGURES

FIG. 1A and FIG. 1B each schematically show an apparatus, according to an embodiment.

FIG. 2 schematically shows a controller of the apparatus, according to an embodiment.

FIG. 9A-FIG. 9C schematically show arrangements of the detectors in the image sensor, according to some embodiments.

FIG. 22 shows another flowchart summarizing and generalizing an operation of the apparatus, according to an embodiment.

DETAILED DESCRIPTION

Figure 3A:
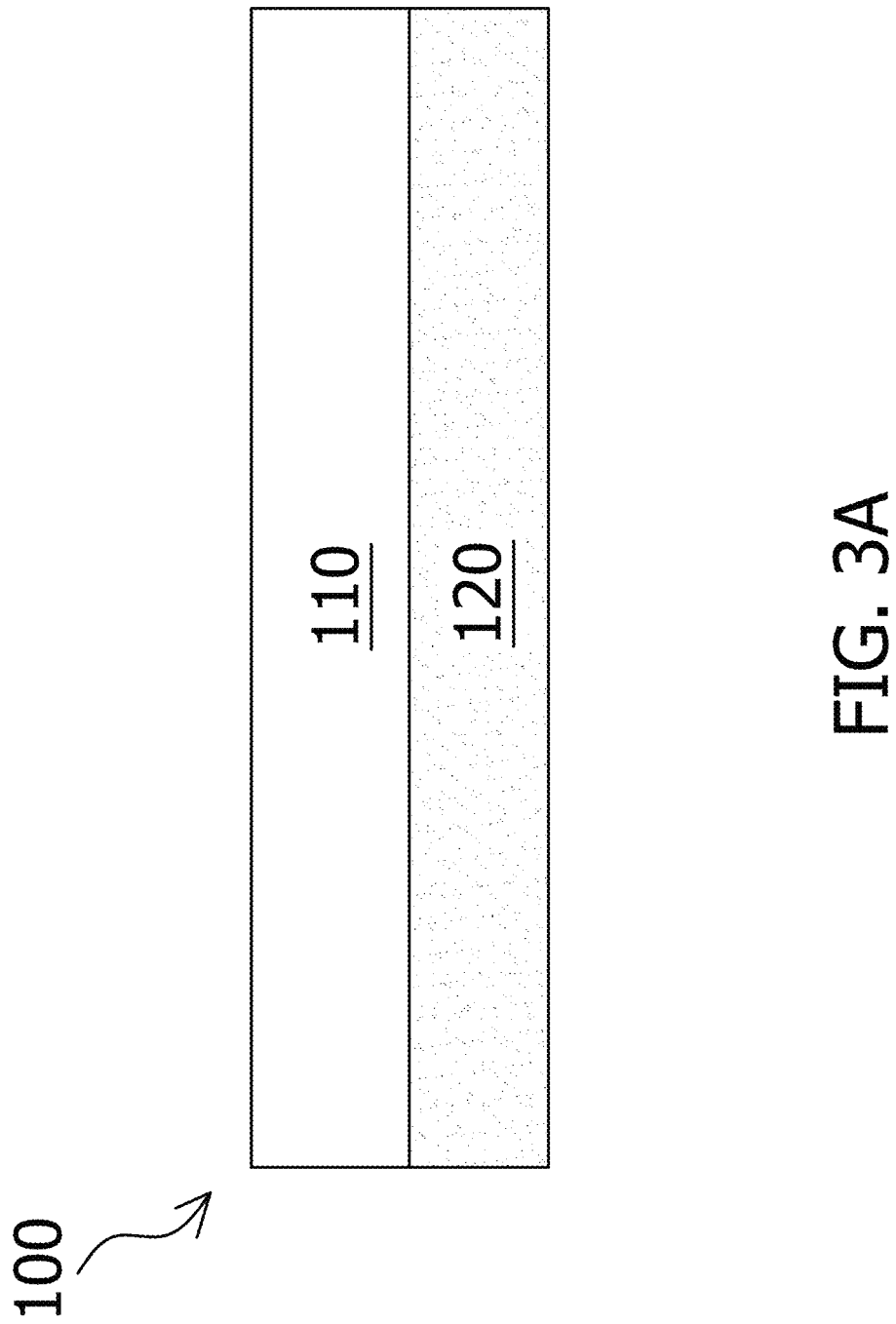
FIG. 3A schematically shows a cross-sectional view of a radiation detector of an image sensor of the apparatus, according to an embodiment.

FIG. 1A and FIG. 1B each schematically show an apparatus 10, according to an embodiment. The apparatus 10 comprises a first radiation source 12, a second radiation source 14, and an image sensor 9000. The apparatus 10 may comprise one or more additional radiation sources.

The first radiation source 12 is configured to produce a first divergent radiation beam 11 toward an object 50. The second radiation source 14 is configured to produce a second divergent radiation beam 13 toward the object 50.

The image sensor 9000 may capture an image of a portion of the object 50 with the first divergent radiation beam 11 or the second divergent radiation beam 13. The image sensor 9000, the first radiation source 12 and the second radiation source 14 are configured to rotate around the object 50 about one or more axes, and relative positions among the image sensor 9000, the first radiation source 12 and the second radiation source 14 are fixed during rotation around the object 50. For example, the image sensor 9000, the first radiation source 12 and the second radiation source 14 may be mounted on a rigid frame 15.

According to an embodiment, the first radiation source 12 and the second radiation source 14 may each be an X-ray source, or a gamma ray source. The object 50 may be a person or a container.

FIG. 1A and FIG. 1B show the positions of the first radiation source 12, the second radiation source 14, and the image sensor 9000 relative to the object 50, respectively before and after the first radiation source 12, the second radiation source 14, and the image sensor 9000 are collectively rotated around the object 50 by such an extent that the first radiation source 12 in FIG. 1A and the second radiation source 14 in FIG. 1B are at the same radiating position relative to the object 50. The image sensor 9000 is at different positions relative to the object 50 in FIG. 1A and FIG. 1B.

The first radiation source 12 is activated in FIG. 1A and the first divergent radiation beam 11 is directed toward the object 50. The image sensor 9000 in FIG. 1A may capture an image of a portion of the object 50 with the first divergent radiation beam 11.

The second radiation source 14 is activated in FIG. 1B and the second divergent radiation beam 13 is directed toward the object 50. The image sensor 9000 in FIG. 1B may capture an image of another portion of the object 50 with the second divergent radiation beam 13.

The apparatus 10 may comprise a shutter 22 as shown in FIG. 1, according to an embodiment. The shutter 22 may be configured to controllably block the first divergent radiation beam 11 from reaching the object 50, and to controllably block the second divergent radiation beam 13 from reaching the object 50. The shutter 22 may have one or more openings. The shutter 22 may have a fixed position relative to the first radiation source 12, the second radiation source 14 and the image sensor 9000. Namely, the shutter 22 may rotate with the first radiation source 12, the second radiation source 14 and the image sensor 9000 with respect to the object 50.

The apparatus 10 may comprise a controller 20, as schematically shown in FIG. 2, according to an embodiment. The controller 20 is configured to activate and deactivate the first radiation source 12 independently from the second radiation source 14, and configured to activate and deactivate the second radiation source 14 independently from the first radiation source 12. Here, activating a radiation source may involve causing it to produce radiation; deactivating a radiation source may involve causing it not to produce radiation. The controller 20 may be electrically connected with the first radiation source 12 and the second radiation source 14. In an example, the controller 20 activates and deactivates the first radiation source 12 and the second radiation source 14 by respectively starting and stopping supplying power to them.

The image sensor 9000 may have a plurality of radiation detectors 100. The radiation detectors 100 may be spaced apart from one another. FIG. 3A schematically shows a cross-sectional view of one radiation detector 100 of the image sensor 9000, according to an embodiment. The radiation detector 100 may include a radiation absorption layer 110 and an electronics layer 120 (e.g., an ASIC) for processing or analyzing electrical signals which incident radiation generates in the radiation absorption layer 110. In an embodiment, the radiation detector 100 does not comprise a scintillator. The radiation absorption layer 110 may include a semiconductor material such as silicon, germanium, GaAs, CdTe, CdZnTe, or a combination thereof. The semiconductor may have a high mass attenuation coefficient for the radiation produced by the radiation sources in the apparatus 10.

Figure 3B:
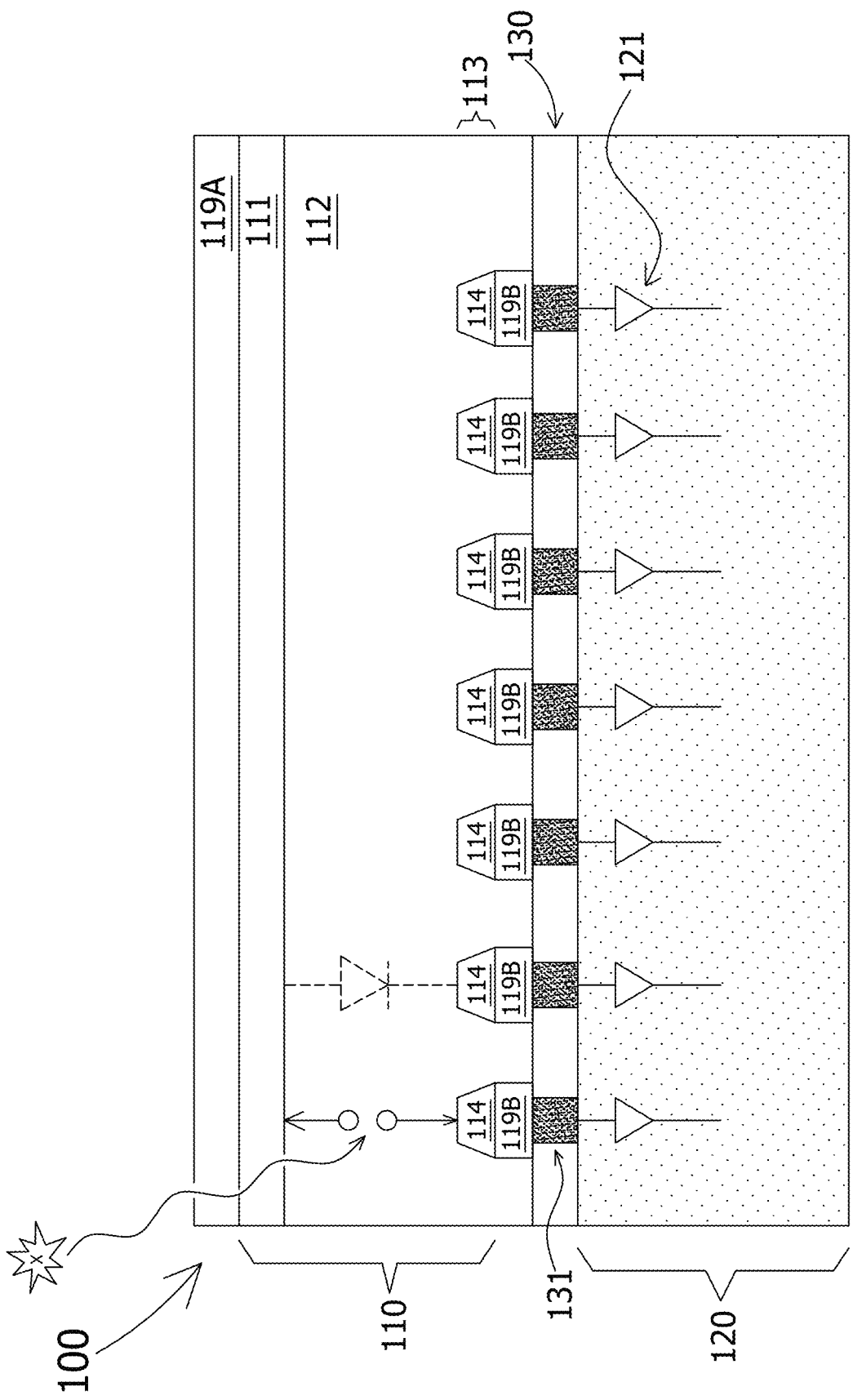
FIG. 3B schematically shows a detailed cross-sectional view of the radiation detector, according to an embodiment.

As shown in a detailed cross-sectional view of the radiation detector 100 in FIG. 3B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 3B, each of the discrete regions 114 of the second doped region 113 forms a diode with the first doped region 111 and the optional intrinsic region 112. Namely, in the example in FIG. 3B, the radiation absorption layer 110 has a plurality of diodes having the first doped region 111 as a shared electrode. The first doped region 111 may also have discrete portions.

When a particle of radiation hits the radiation absorption layer 110 including diodes, the particle of radiation may be absorbed and generate one or more charge carriers by a number of mechanisms. A particle of radiation may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single particle of radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of radiation incident around the footprint of one of these discrete regions 114 are not substantially shared with another of these discrete regions 114. A pixel (also called a sensing element) 150 associated with a discrete region 114 may be an area around the discrete region 114 in which substantially all (more than 98%, more than 99.5%, more than 99.9%, or more than 99.99% of) charge carriers generated by a particle of radiation incident therein flow to the discrete region 114. Namely, less than 2%, less than 1%, less than 0.1%, or less than 0.01% of these charge carriers flow beyond the pixel.

Figure 3C:
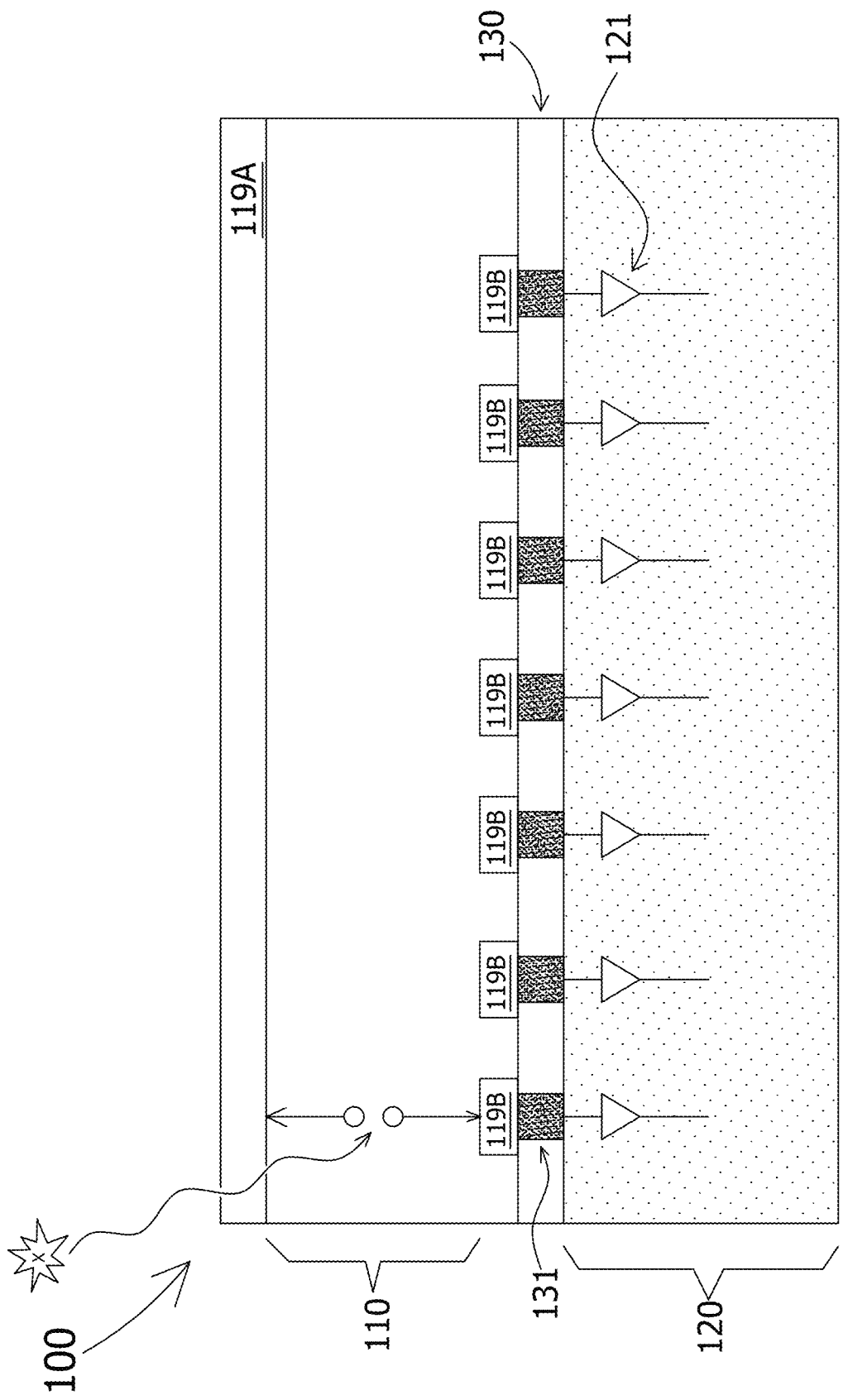
FIG. 3C schematically shows an alternative detailed cross-sectional view of the radiation detector, according to an embodiment.

As shown in an alternative detailed cross-sectional view of the radiation detector 100 in FIG. 3C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation produced by the radiation sources in the apparatus 10.

When a particle of radiation hits the radiation absorption layer 110 including a resistor but not diodes, it may be absorbed and generate one or more charge carriers by a number of mechanisms. A particle of radiation may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single particle of radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by particles of radiation incident on the radiation absorption layer 110. The electronic system 121 may include an analog circuitry such as a filter network, amplifiers, integrators, and comparators, or a digital circuit such as a microprocessor and a memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 4:
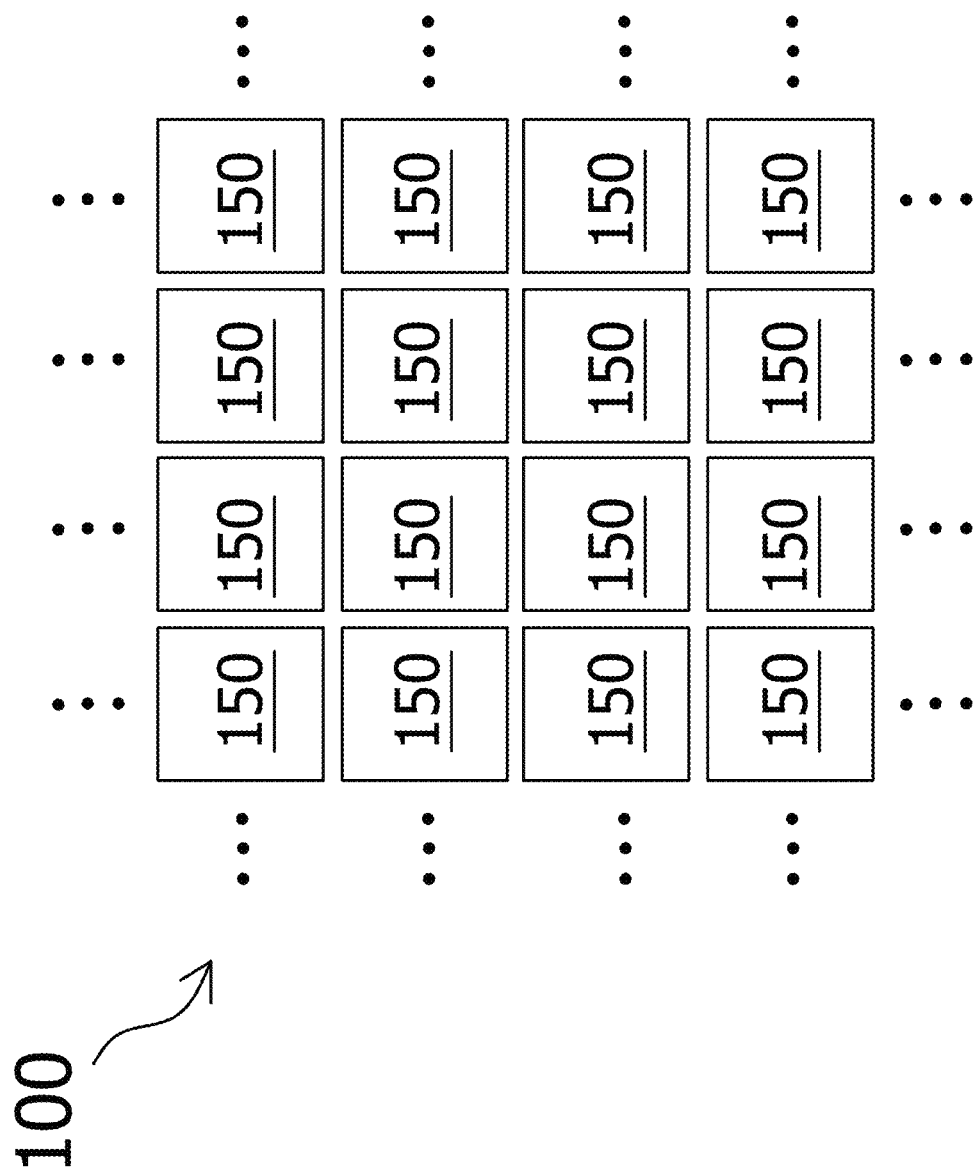
FIG. 4 schematically shows that the radiation detector may have an array of pixels, according to an embodiment.

FIG. 4 schematically shows that the radiation detector 100 may have an array of pixels 150. The array may be a rectangular array, a honeycomb array, a hexagonal array or any other suitable array. Each pixel 150 may be configured to detect a particle of radiation incident thereon, measure the energy of the particle of radiation, or both. For example, each pixel 150 may be configured to count numbers of particles of radiation incident thereon whose energy falls in a plurality of bins, within a period of time. All the pixels 150 may be configured to count the numbers of particles of radiation incident thereon within a plurality of bins of energy within the same period of time. Each pixel 150 may have its own analog-to-digital converter (ADC) configured to digitize an analog signal representing the energy of an incident particle of radiation into a digital signal. The ADC may have a resolution of 10 bits or higher. Each pixel 150 may be configured to measure its dark current, such as before or concurrently with each particle of radiation incident thereon. Each pixel 150 may be configured to deduct the contribution of the dark current from the energy of the particle of radiation incident thereon. The pixels 150 may be configured to operate in parallel. For example, when one pixel 150 measures an incident particle of radiation, another pixel 150 may be waiting for a particle of radiation to arrive. The pixels 150 may be but do not have to be individually addressable.

Figure 5A:
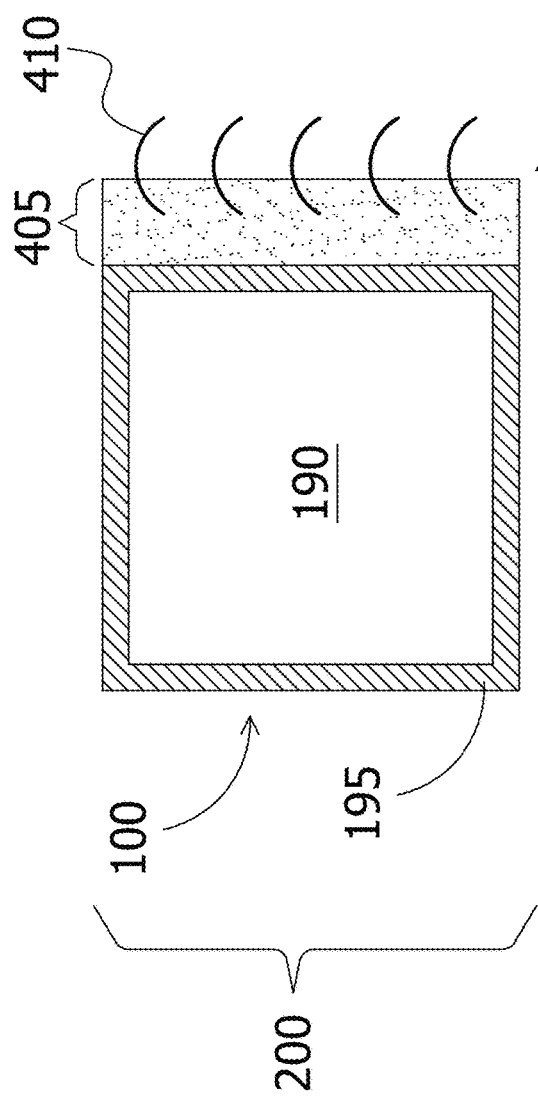
FIG. 5A schematically shows a top view of a package including the radiation detector and a printed circuit board (PCB).
Figure 5B:
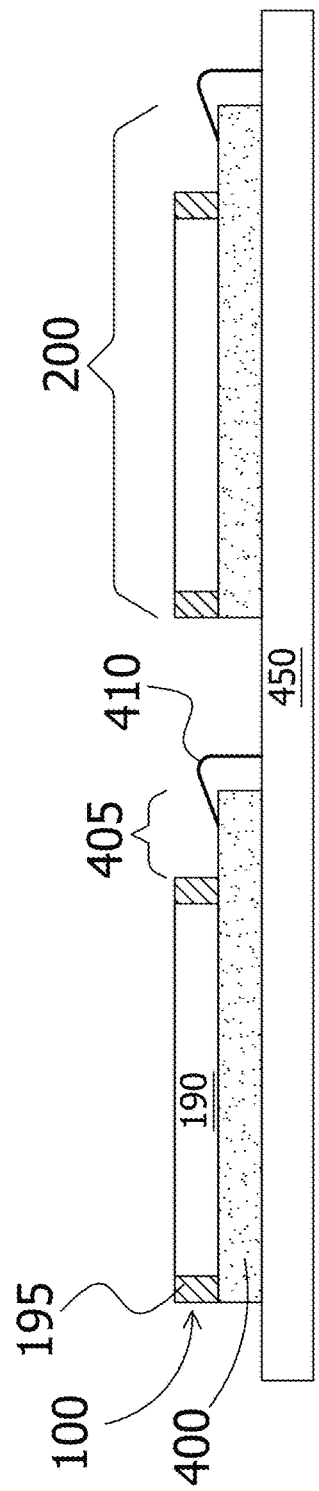
FIG. 5B schematically shows a cross-sectional view of the image sensor, where a plurality of the packages of FIG. 5A are mounted to another PCB.

The radiation detectors of the image sensors 9000 may be arranged in any suitable fashion. FIG. 5A and FIG. 5B show an example of the arrangement of the radiation detectors in the image sensor 9000. One or more of the radiation detectors 100 may be mounted on a printed circuit board (PCB) 400. The term "PCB" as used herein is not limited to a particular material. For example, a PCB may include a semiconductor. The radiation detector 100 is mounted to the PCB 400. The wiring between the radiation detectors 100 and the PCB 400 is not shown for the sake of clarity. The PCB 400 and the radiation detectors 100 mounted thereon may be called a package 200. The PCB 400 may have an area not covered by the radiation detectors 100 (e.g., an area for accommodating bonding wires 410). Each of the radiation detectors 100 may have an active area 190, which is where the pixels 150 are located. Each of the radiation detectors 100 may have a perimeter zone 195 near the edges.

The perimeter zone 195 has no pixels and particles of radiation incident on the perimeter zone 195 are not detected.

FIG. 5B schematically shows that the image sensor 9000 may have a system PCB 450 with multiple packages 200 mounted on it. The image sensor 9000 may include one or more such system PCBs 450. The electrical connection between the PCBs 400 in the packages 200 and the system PCB 450 may be made by bonding wires 410. In order to accommodate the bonding wires 410 on the PCB 400, the PCB 400 has an area 405 not covered by the radiation detectors 100. In order to accommodate the bonding wires 410 on the system PCB 450, the packages 200 have gaps in between. The active areas 190 of the radiation detectors 100 in the image sensor 9000 are collectively called the active area of the image sensor 9000. The other areas of the image sensor 9000, radiation incident on which cannot be detected by the image sensor 9000, such as the perimeter zones 195, the area 405 or the gaps between the packages 200, are collectively called the dead zone of the image sensor 9000.

Figure 6B:
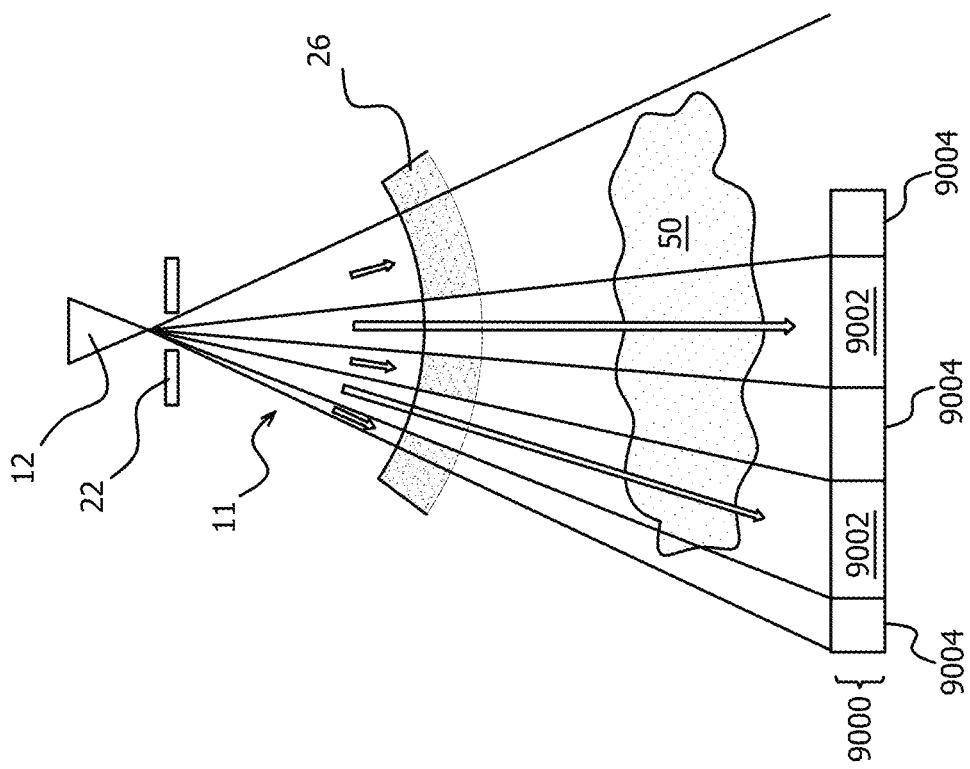
FIG. 6A and FIG. 6B schematically show a first mask of the apparatus, according to an embodiment.
Figure 6A:
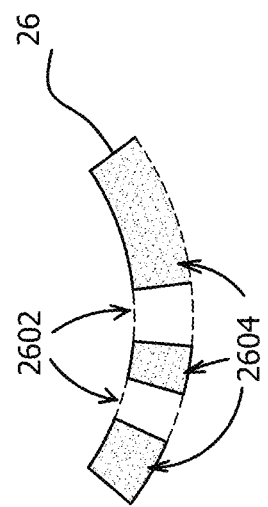

FIG. 6A and FIG. 6B schematically show that the apparatus 10 may have a first mask 26. The first mask 26 may have a plurality of radiation transmitting zones 2602 and a radiation blocking zone 2604, according to an embodiment. FIG. 6B schematically shows that the radiation blocking zone 2604 is configured to block a portion of the first divergent radiation beam 11 that would otherwise incident on the dead zone 9004 of the image sensor 9000 through the object 50, and the radiation transmitting zones 2602 are configured to transmit at least a portion of the first divergent radiation beam 11 that would incident on the active areas 9002 of the image sensor 9000, according to an embodiment.

According to an embodiment, the first mask 26 may be made of materials such as lead. The radiation transmitting zones 2602 of the first mask 26 may be a plurality of holes. The radiation blocking zone of the first mask 26 may be the area thereof except those holes.

According to an embodiment, the first mask 26 may be positioned between the first radiation source 12 and the object 50. The first mask 26 may reduce the dose of the radiation the object 50 receives.

Figure 6D:
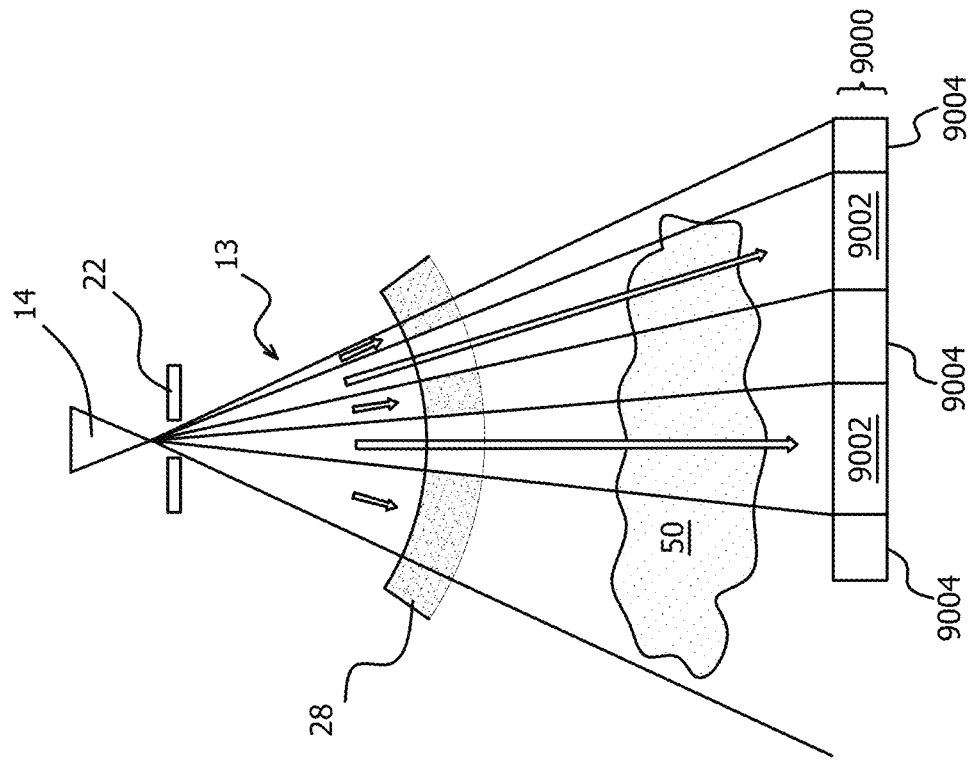
FIG. 6C and FIG. 6D schematically show a second mask of the apparatus, according to an embodiment.
Figure 6C:
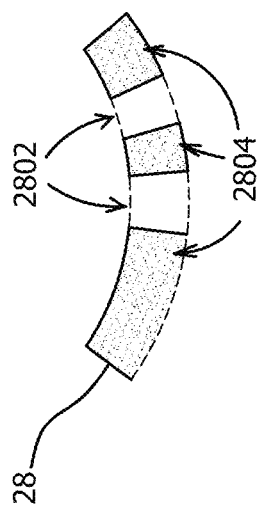

FIG. 6C and FIG. 6D schematically show that the apparatus 10 may have a second mask 28. The second mask 28 may have a plurality of radiation transmitting zones 2802 and a radiation blocking zone 2804, according to an embodiment. FIG. 6D schematically shows that the radiation blocking zone 2804 is configured to block a portion of the second divergent radiation beam 13 that would otherwise incident on the dead zone 9004 of the image sensor 9000 through the object 50, and the radiation transmitting zones 2802 are configured to transmit at least a portion of the second divergent radiation beam 13 that would incident on the active areas 9002 of the image sensor 9000, according to an embodiment.

According to an embodiment, the second mask 28 may be made of materials such as lead. The radiation transmitting zones 2802 of the second mask 28 may be a plurality of holes. The radiation blocking zone of the second mask 28 may be the area thereof except those holes.

According to an embodiment, the second mask 28 may be positioned between the second radiation source 14 and the object 50. The second mask 28 may reduce the dose of the radiation the object 50 receives.

Figure 7:
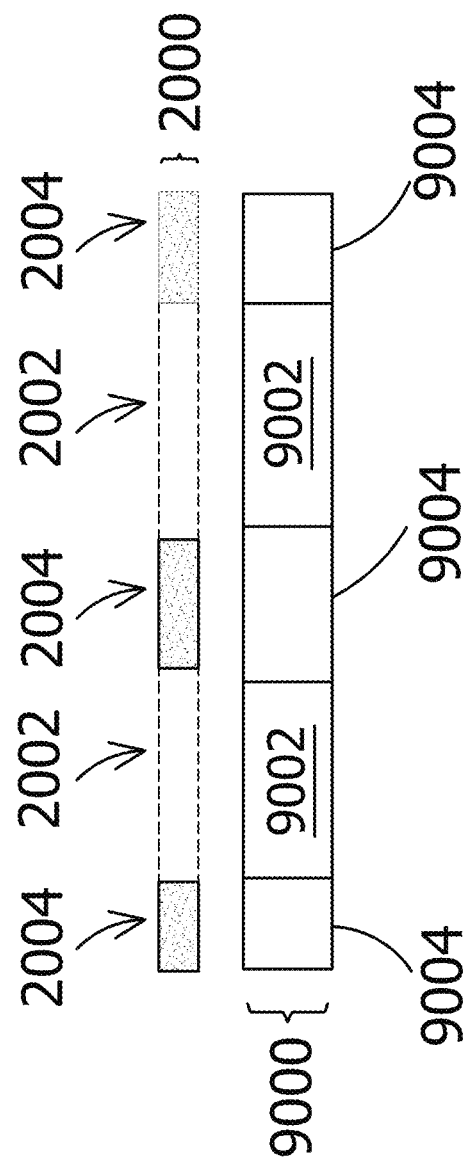
FIG. 7 schematically shows a collimator of the image sensor, according to an embodiment.

FIG. 7 schematically shows that the image sensor 9000 may comprise a collimator 2000. The collimator 2000 comprises a plurality of radiation transmitting zones 2002 and a radiation blocking zone 2004, according to an embodiment. The radiation blocking zone 2004 substantially blocks radiation that would otherwise incident on the dead zone 9004 of the image sensor 9000, and the radiation transmitting zones 2002 allow at least a portion of radiation that would incident on the active areas 9002 of the image sensor 9000 to pass. The radiation transmitting zones 2002 may be holes through the collimator 2000 and the rest of the collimator 2000 may function as the radiation blocking zone 2004. The collimator 2000 may be disposed close to the image sensor 9000. The radiation transmitting zones 2002 may have a slightly different sizes or positions from those of the active areas 9002 of the image sensor 9000.

Figure 8A:
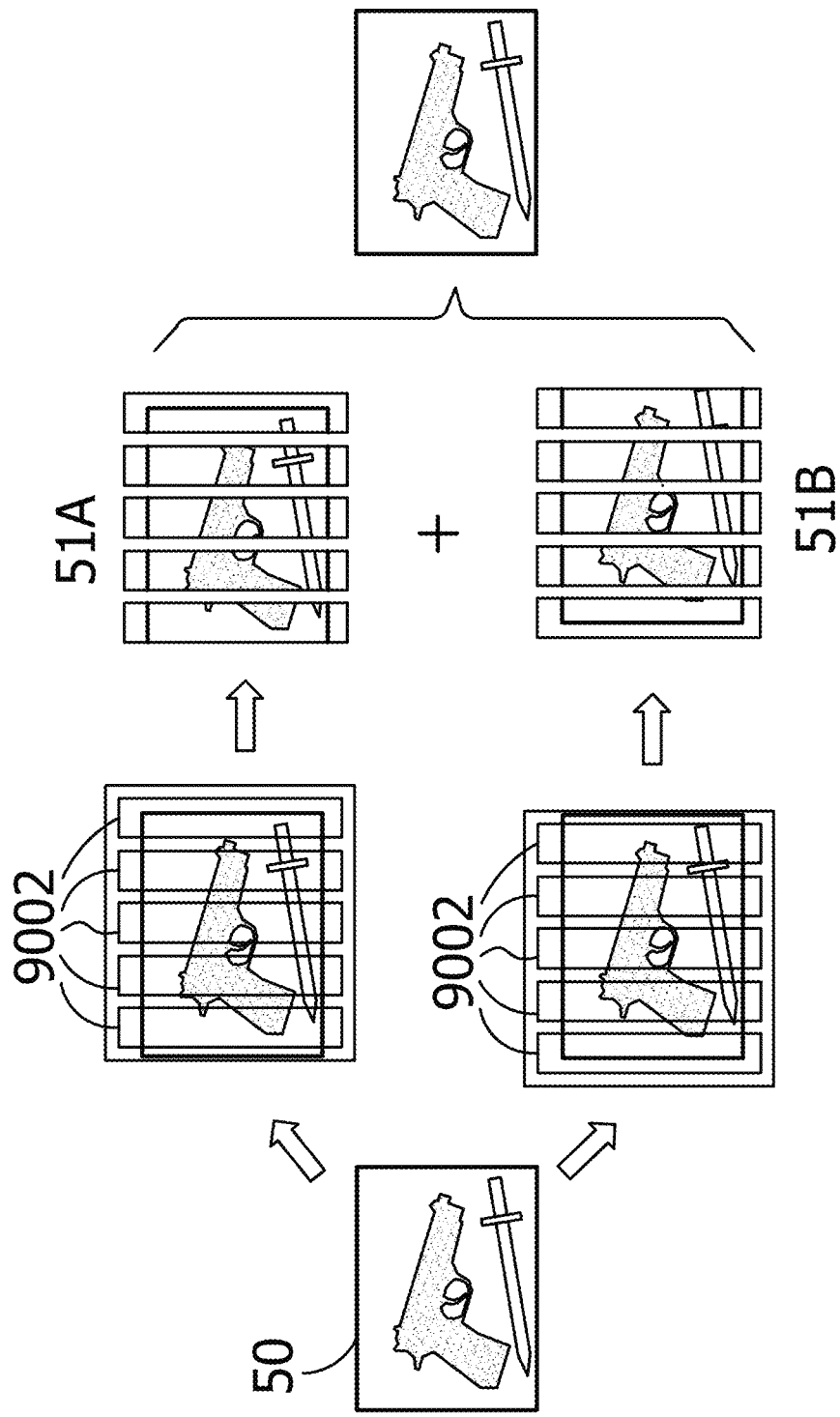
FIG. 8A schematically shows the image of an object can be formed by stitching images of multiple different portions of an object, according to an embodiment.

As schematically shown in FIG. 8A, the image sensor 9000 captures a portion image 51A of a portion of the object 50 with the first divergent radiation beam 11, when the image sensor 9000, the first radiation source 12 and the second radiation source 14 are at their respective positions relative to the object 50 as shown in FIG. 1A.

The image sensor 9000, the first radiation source 12 and the second radiation source 14 are collectively rotated relative to the object 50 to their respective positions relative to the object 50 as shown in FIG. 1B, where the image sensor 9000 captures a portion image 51B of another portion of the object 50 with the second divergent radiation beam 13.

The image sensor 9000 then forms a stitched image of the object 50 by stitching the portion image 51A and the portion image 51B. The portion images 51A and 51B may partially overlap to facilitate stitching.

Figure 8B:
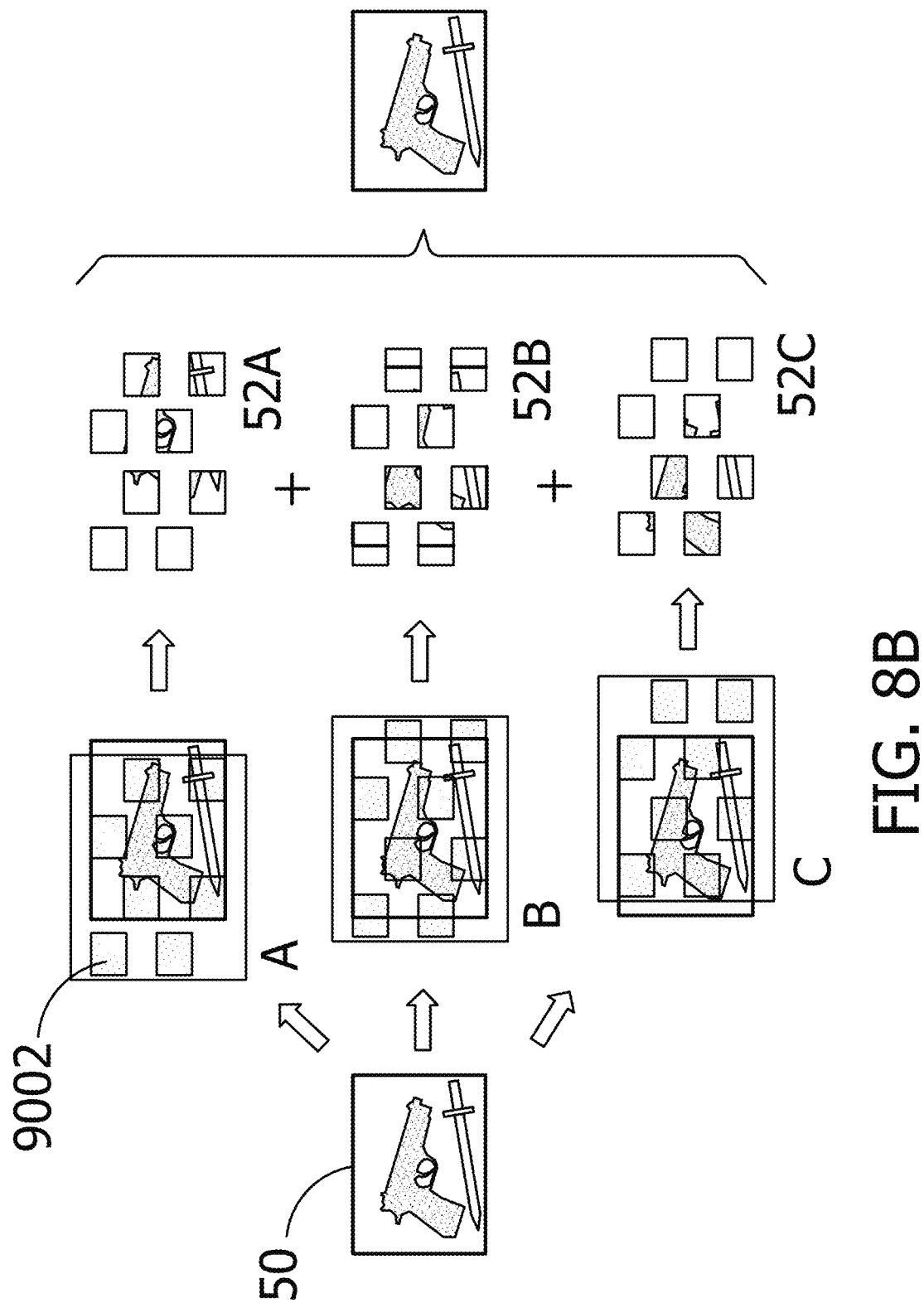
FIG. 8B schematically shows the image of an object can be formed by stitching images of multiple different portions of an object, according to an embodiment.

According to an embodiment, the apparatus 10 may include more than two radiation sources. FIG. 8B schematically shows an example where the apparatus 10 has three radiation sources. The image sensors 9000 captures three portion images 52A, 52B and 52C of different portions of the object 50 respectively at three different positions A, B and C relative to the object 50, respectively with divergent radiation beams of radiation from the three radiation sources. The image sensor 9000 forms a stitched image of the object 50 by stitching the portion images 52A, 52B and 52C. The portion images 52A, 52B and 52C may partially overlap to facilitate stitching. The radiation sources may be staggered, namely not disposed along a straight line.

The radiation detectors 100 may be arranged in a variety of ways in the image sensor 9000. FIG. 9A schematically shows one arrangement, according to an embodiment, where the radiation detectors 100 are arranged in staggered rows. For example, radiation detectors 100A and 100B are in the same row, aligned in the Y direction, and uniform in size; radiation detectors 100C and 100D are in the same row, aligned in the Y direction, and uniform in size. Radiation detectors 100A and 100B are staggered in the X direction with respect to radiation detectors 100C and 100D. According to an embodiment, a distance X2 between two neighboring radiation detectors 100A and 100B in the same row is greater than a width X1 (i.e., dimension in the X direction, which is the extending direction of the row) of one detector in the same row and is less than twice the width X1. Radiation detectors 100A and 100E are in a same column, aligned in the X direction, and uniform in size; a distance Y2 between two neighboring radiation detectors 100A and 100E in the same column is less than a width Y1 (i.e., dimension in the Y direction) of one detector in the same column.

FIG. 9B schematically shows another arrangement, according to an embodiment, where the radiation detectors 100 are arranged in a rectangular grid. For example, the radiation detectors 100 may include radiation detectors 100A, 100B, 100E and 100F as arranged exactly in FIG. 9A, without radiation detectors 100C, 100D, 100G, or 100H in FIG. 9A.

Other arrangements may also be possible. For example, in FIG. 9C, the radiation detectors 100 may span the whole width of the image sensor 9000 in the X-direction, with a distance Y2 between two neighboring radiation detectors 100 being less than a width of one detector Y1.

According to an embodiment, the radiation sources (e.g., 12 and 14) and the image sensor 9000 may collectively rotate around the object about multiple axes.

Figure 10:
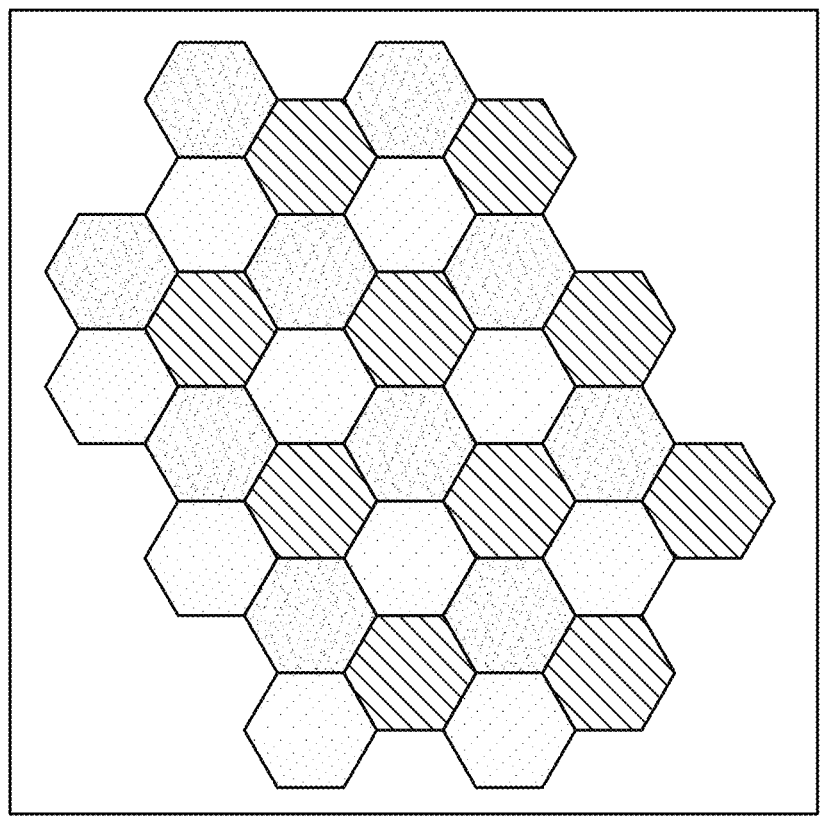
FIG. 10 schematically shows detectors that are hexagonal in shape, according to an embodiment.

The radiation detectors 100 in the image sensor 9000 have any suitable sizes and shapes. According to an embodiment (e.g., in FIG. 9A-FIG. 9C), at least some of the radiation detectors 100 are rectangular in shape. According to an embodiment, as shown in FIG. 10, at least some of the radiation detectors are hexagonal in shape. In such radiation detectors, the radiation detectors and the corresponding collimators that are aligned may have the same shape.

Figure 11:
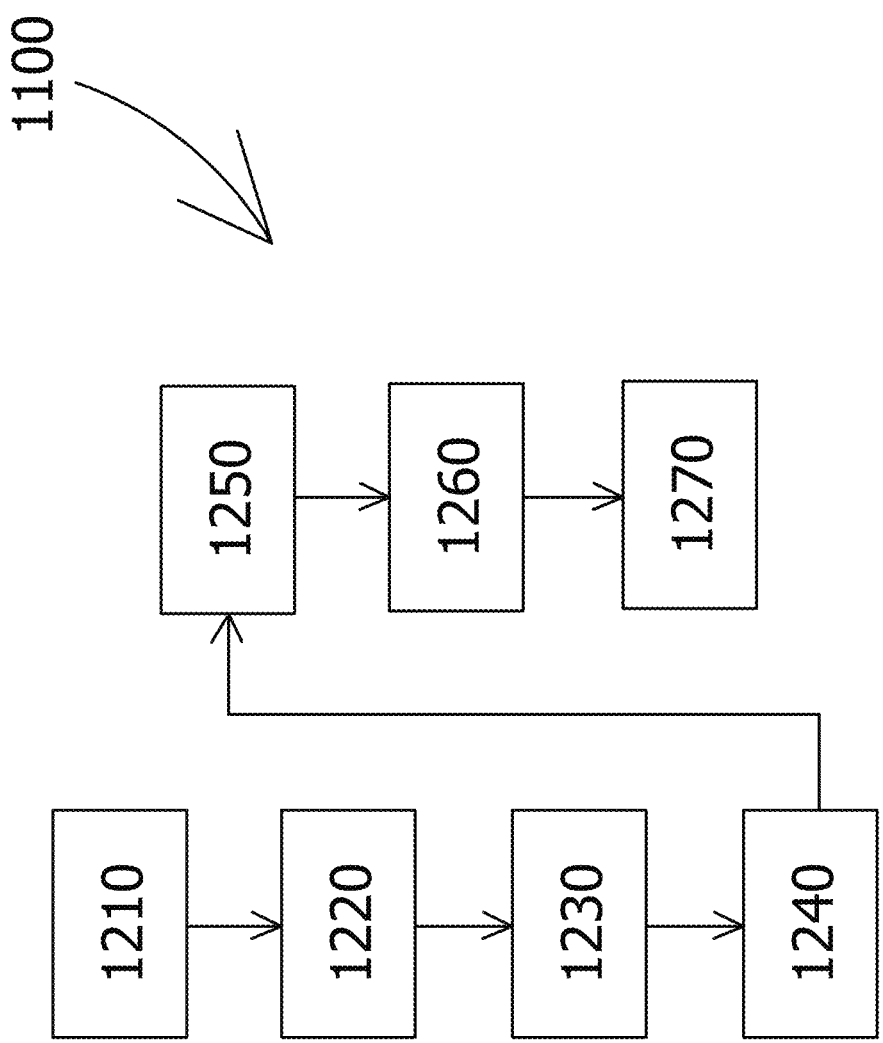
FIG. 11 schematically shows a flowchart of the method using the apparatus, according to an embodiment.

FIG. 11 schematically shows the flowchart 1100 of the method, according to an embodiment. In procedure 1210, the first radiation source 12 is positioned at a relative radiating position with respect to the object 50. In procedure 1220, the first divergent radiation beam 11 is directed toward the object 50. In procedure 1230, a portion image of a first portion of the object 50 is captured using the image sensor 9000 with the first divergent radiation beam 11. In procedure 1240, the second radiation source 14 is positioned at the same relative radiating position with respect to the object 50. In procedure 1250, the second divergent radiation beam 13 is directed toward the object 50. In procedure 1260, a portion image of a second portion of the object 50 is captured using the image sensor 9000 with the second divergent radiation beam 13. In procedure 1270, a stitched image of the object 50 is formed by stitching the portion image of the first portion and the portion image of the second portion. Because relative positions among the image sensor 9000, the first radiation source 12 and the second radiation source 14 are fixed, positioning the first radiation source 12 in procedure 1210 also causes positioning of the second radiation source 14 and the image sensor 9000, and positioning the second radiation source 14 in procedure 1240 also causes positioning of the first radiation source 12 and the image sensor 9000.

Radiation produced by the first radiation source 12 may be blocked from reaching the object 50 while the first radiation source 12 is not at the relative radiating position, and radiation produced by the second radiation source 14 may be blocked from reaching the object 50 while the second radiation source 14 is not at the relative radiating position. For example, the radiation may be blocked using the shutter 22.

The first radiation source 12 may remain deactivated while it is not at the relative radiating position, and the second radiation source 14 may be deactivated while it is not at the relative radiating position.

Figure 12A:
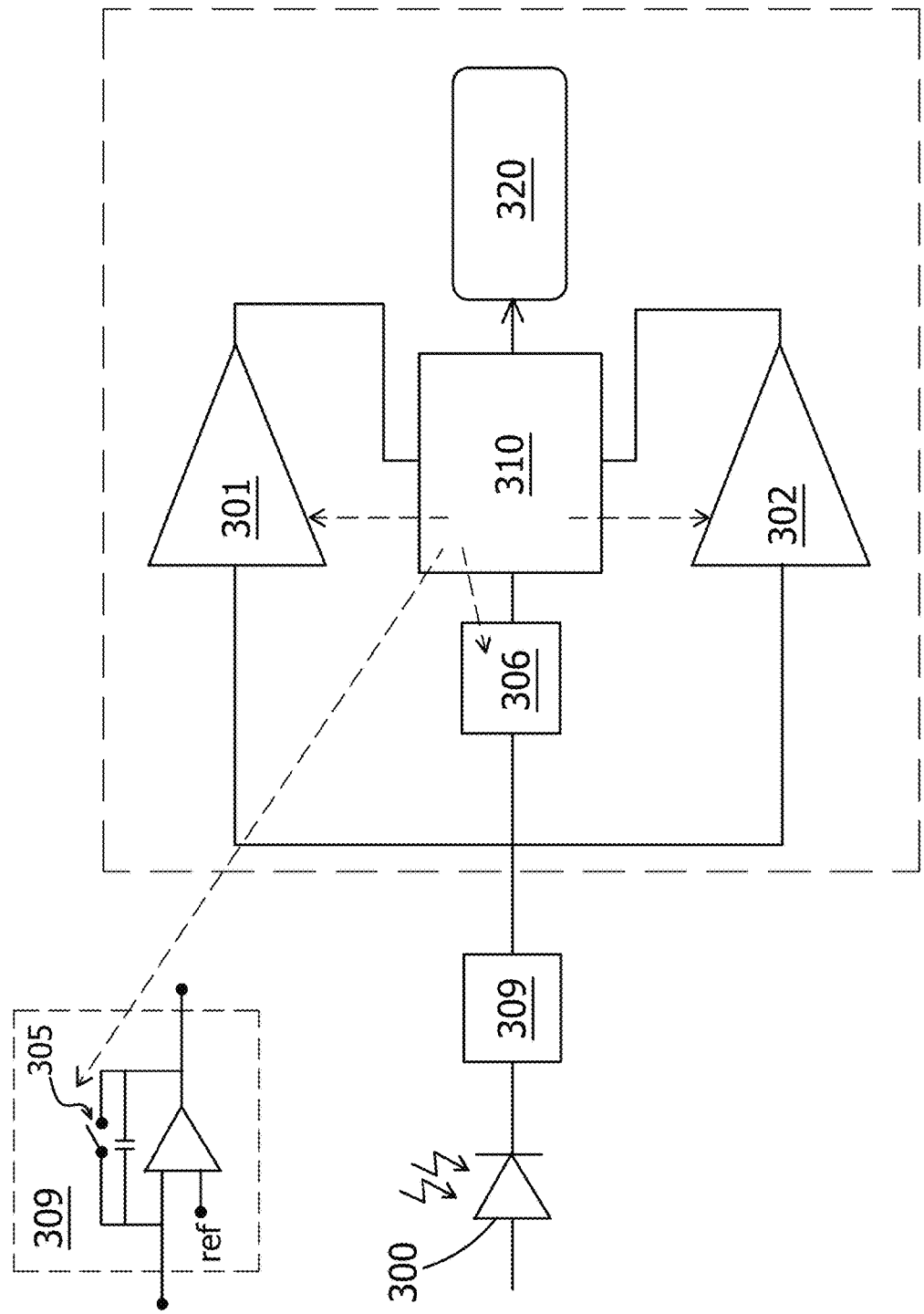
FIG. 12A and FIG. 12B each show a component diagram of an electronic system of the detector in FIG. 3A, FIG. 3B and FIG. 3C, according to an embodiment.
Figure 12B:
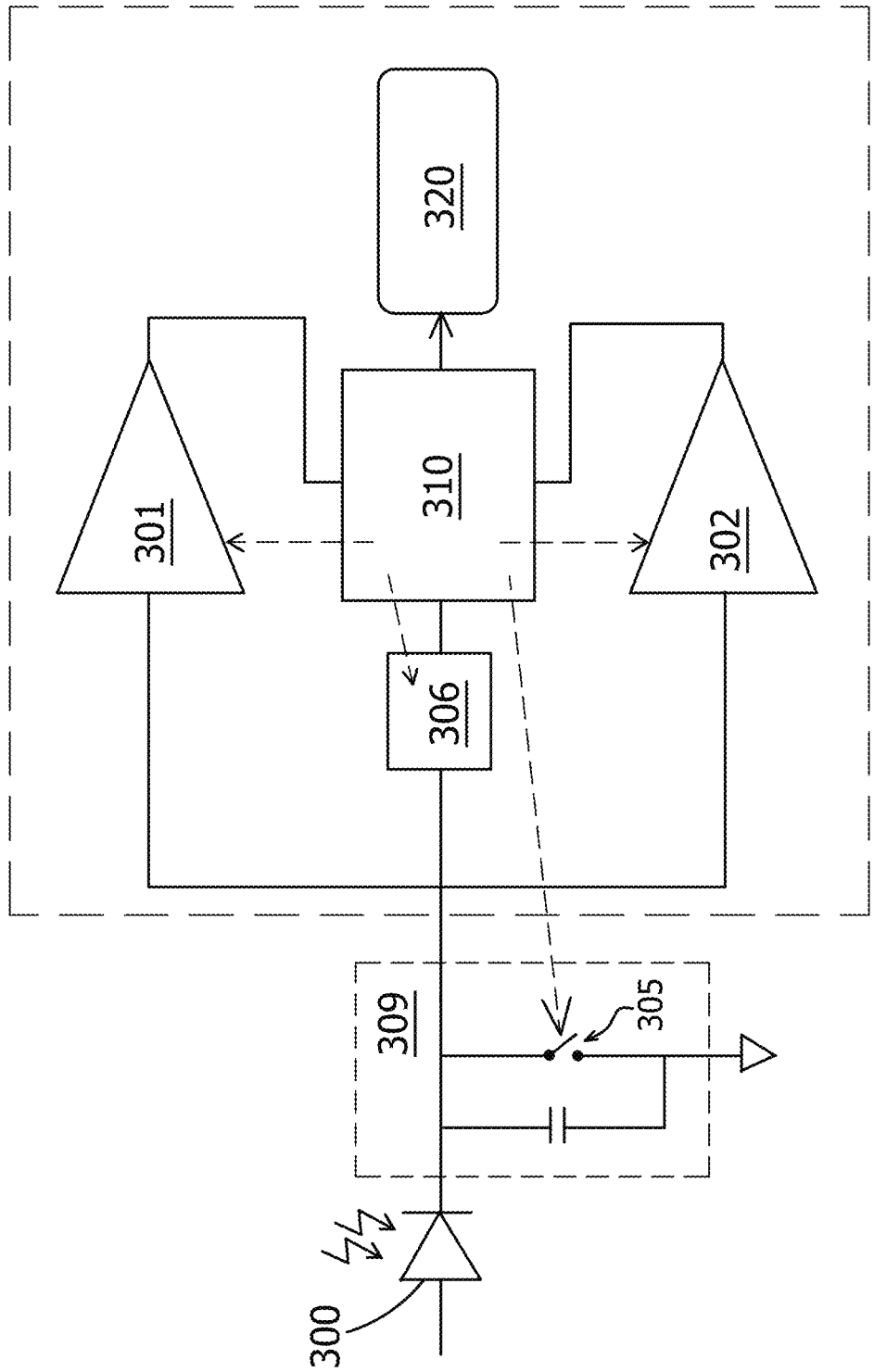

FIG. 12A and FIG. 12B each show a component diagram of the electronic system 121, according to an embodiment. The electronic system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 configured as a continuous comparator reduces the chance that the system 121 misses signals generated by an incident particle of radiation. The first voltage comparator 301 configured as a continuous comparator is especially suitable when the incident radiation intensity is relatively high. The first voltage comparator 301 may be a clocked comparator, which has the benefit of lower power consumption. The first voltage comparator 301 configured as a clocked comparator may cause the system 121 to miss signals generated by some incident particles of radiation. When the incident radiation intensity is low, the chance of missing an incident particle of radiation is low because the time interval between two successive particles is relatively long. Therefore, the first voltage comparator 301 configured as a clocked comparator is especially suitable when the incident radiation intensity is relatively low. The first threshold may be 5-10%, 10%-20%, 20-30%, 30-40% or 40-50% of the maximum voltage one incident particle of radiation may generate in the diode or the resistor. The maximum voltage may depend on the energy of the incident particle of radiation (i.e., the wavelength of the incident radiation), the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activated or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, |x|=x, if x≥0, and |x|=−x, if x<0. The second threshold may be 200%-300% of the first threshold. The second threshold may be at least 50% of the maximum voltage one incident particle of radiation may generate in the diode or resistor. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident radiation. However, having a high speed is often at the cost of power consumption.

The counter 320 is configured to register a number of particles of radiation reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cutting off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 13:
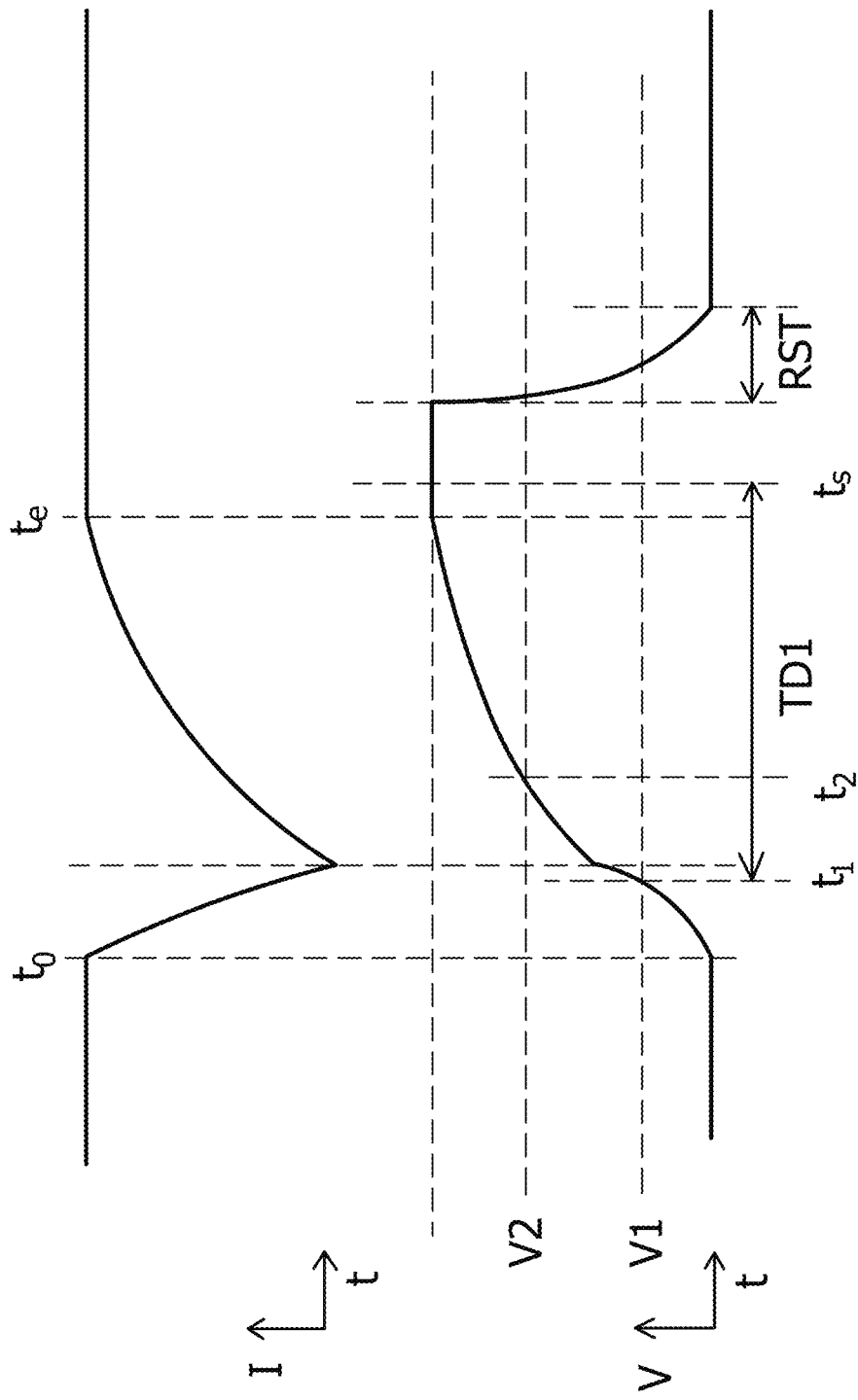
FIG. 13 schematically shows a temporal change of the electric current flowing through an electrode (upper curve) of a diode or an electrical contact of a resistor of a radiation absorption layer exposed to radiation, the electric current caused by charge carriers generated by a particle of radiation incident on the radiation absorption layer, and a corresponding temporal change of the voltage of the electrode (lower curve), according to an embodiment.

The system 121 may include an integrator 309 electrically connected to the electrode of the diode 300 or which electrical contact, wherein the integrator is configured to collect charge carriers from the electrode. The integrator can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 13, between $t_0$ to $t_1$, or $t_1$-$t_2$). After the integration period has expired, the capacitor voltage is sampled and then reset by a reset switch. The integrator can include a capacitor directly connected to the electrode.

FIG. 13 schematically shows a temporal change of the electric current flowing through the electrode (upper curve) caused by charge carriers generated by a particle of radiation incident on the diode or the resistor, and a corresponding temporal change of the voltage of the electrode (lower curve). The voltage may be an integral of the electric current with respect to time. At time $t_0$, the particle of radiation hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 causes the number registered by the counter 320 to increase by one. At time $t_e$, all charge carriers generated by the particle of radiation drift out of the radiation absorption layer 110. At time $t_s$, the time delay TD1 expires. In the example of FIG. 13, time $t_s$ is after time $t_e$; namely TD1 expires after all charge carriers generated by the particle of radiation drift out of the radiation absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by a particle of radiation, which relates to the energy of the particle of radiation. The controller 310 may be configured to determine the energy of the particle of radiation based on voltage the voltmeter 306 measures. One way to determine the energy is by binning the voltage. The counter 320 may have a sub-counter for each bin. When the controller 310 determines that the energy of the particle of radiation falls in a bin, the controller 310 may cause the number registered in the sub-counter for that bin to increase by one. Therefore, the system 121 may be able to detect a radiation image and may be able to resolve particle of radiation energies of each particle of radiation.

After TD1 expires, the controller 310 connects the electrode to an electric ground for a reset period RST to allow charge carriers accumulated on the electrode to flow to the ground and reset the voltage. After RST, the system 121 is ready to detect another incident particle of radiation. Implicitly, the rate of incident particles of radiation the system 121 can handle in the example of FIG. 13 is limited by 1/(TD1+RST). If the first voltage comparator 301 has been deactivated, the controller 310 can activate it at any time before RST expires. If the controller 310 has been deactivated, it may be activated before RST expires.

Figure 14:
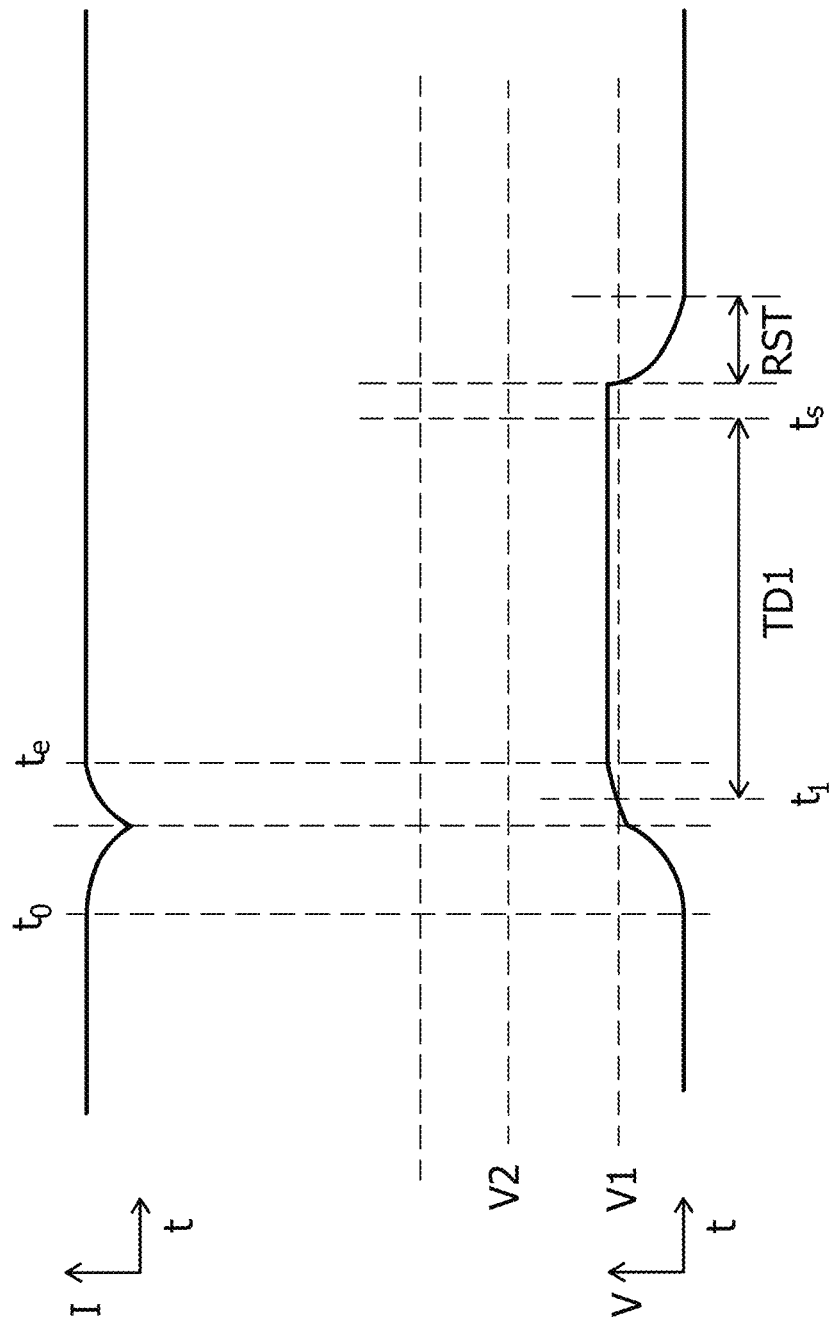
FIG. 14 schematically shows a temporal change of the electric current flowing through the electrode (upper curve) caused by noise (e.g., dark current), and a corresponding temporal change of the voltage of the electrode (lower curve), in the electronic system operating in the way shown in FIG. 13, according to an embodiment.

FIG. 14 schematically shows a temporal change of the electric current flowing through the electrode (upper curve) caused by noise (e.g., dark current, background radiation, scattered radiations, fluorescent radiations, shared charges from adjacent pixels), and a corresponding temporal change of the voltage of the electrode (lower curve), in the system 121 operating in the way shown in FIG. 13. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 15:
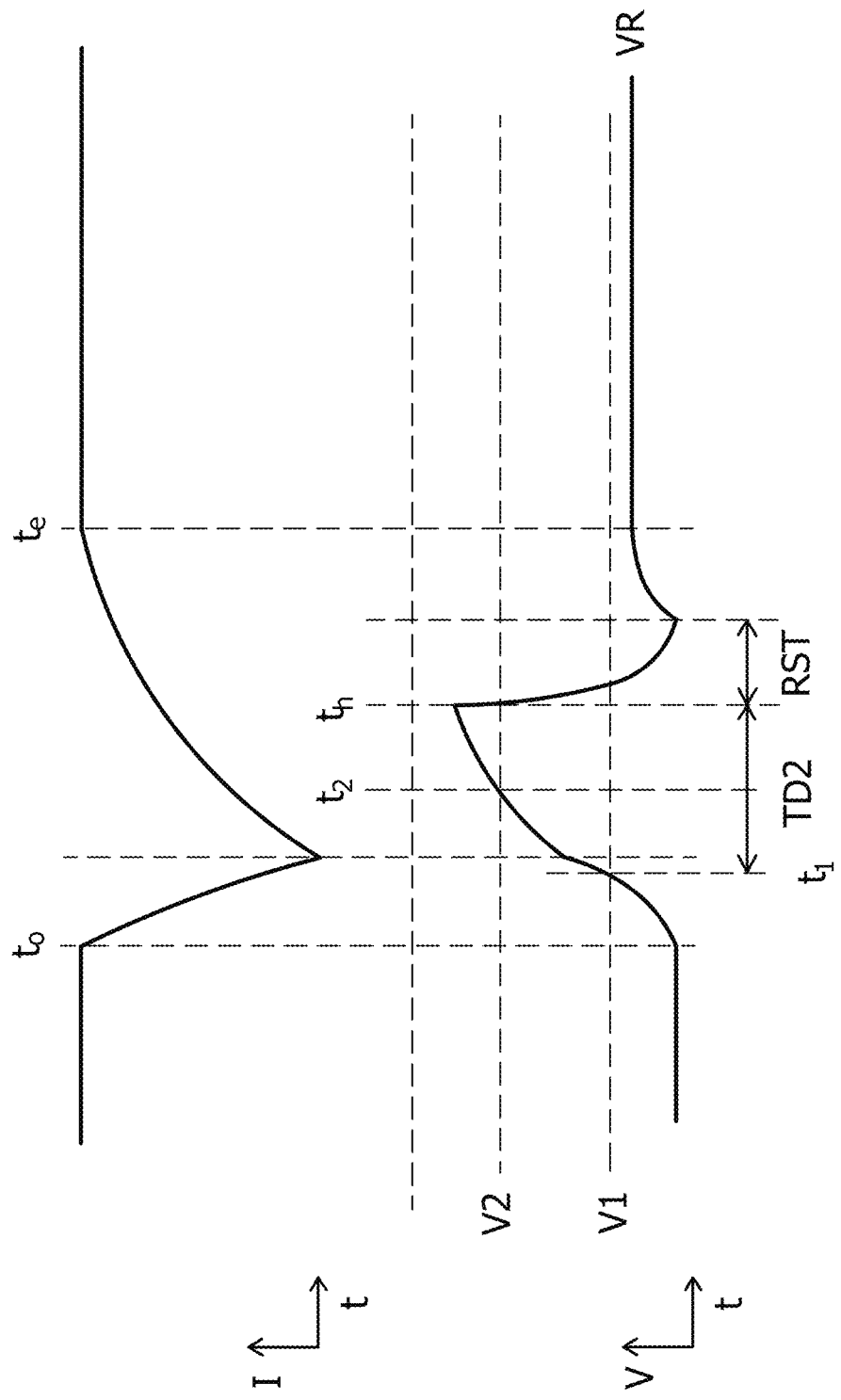
FIG. 15 schematically shows a temporal change of the electric current flowing through an electrode (upper curve) of the radiation absorption layer exposed to radiation, the electric current caused by charge carriers generated by a particle of radiation incident on the radiation absorption layer, and a corresponding temporal change of the voltage of the electrode (lower curve), when the electronic system operates to detect incident particles of radiation at a higher rate, according to an embodiment.

FIG. 15 schematically shows a temporal change of the electric current flowing through the electrode (upper curve) caused by charge carriers generated by a particle of radiation incident on the diode or the resistor, and a corresponding temporal change of the voltage of the electrode (lower curve), when the system 121 operates to detect incident particles of radiation at a rate higher than 1/(TD1+RST). The voltage may be an integral of the electric current with respect to time. At time $t_0$, the particle of radiation hits the diode or the resistor, charge carriers start being generated in the diode or the resistor, electric current starts to flow through the electrode of the diode or the electrical contact of resistor, and the absolute value of the voltage of the electrode or the electrical contact starts to increase. At time $t_1$, the first voltage comparator 301 determines that the absolute value of the voltage equals or exceeds the absolute value of the first threshold V1, and the controller 310 starts a time delay TD2 shorter than TD1, and the controller 310 may deactivate the first voltage comparator 301 at the beginning of TD2. If the controller 310 is deactivated before $t_1$, the controller 310 is activated at $t_1$. During TD2 (e.g., at expiration of TD2), the controller 310 activates the second voltage comparator 302. If during TD2, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the particle of radiation drift out of the radiation absorption layer 110. At time $t_h$, the time delay TD2 expires. In the example of FIG. 15, time $t_h$ is before time $t_e$; namely TD2 expires before all charge carriers generated by the particle of radiation drift out of the radiation absorption layer 110. The rate of change of the voltage is thus substantially non-zero at $t_h$. The controller 310 may be configured to deactivate the second voltage comparator 302 at expiration of TD2 or at $t_2$, or any time in between.

The controller 310 may be configured to extrapolate the voltage at $t_e$ from the voltage as a function of time during TD2 and use the extrapolated voltage to determine the energy of the particle of radiation.

After TD2 expires, the controller 310 connects the electrode to an electric ground for a reset period RST to allow charge carriers accumulated on the electrode to flow to the ground and reset the voltage. In an embodiment, RST expires before $t_e$. The rate of change of the voltage after RST may be substantially non-zero because all charge carriers generated by the particle of radiation have not drifted out of the radiation absorption layer 110 upon expiration of RST before $t_e$. The rate of change of the voltage becomes substantially zero after $t_e$ and the voltage stabilized to a residue voltage VR after $t_e$. In an embodiment, RST expires at or after $t_e$, and the rate of change of the voltage after RST may be substantially zero because all charge carriers generated by the particle of radiation drift out of the radiation absorption layer 110 at $t_e$. After RST, the system 121 is ready to detect another incident particle of radiation. If the first voltage comparator 301 has been deactivated, the controller 310 can activate it at any time before RST expires. If the controller 310 has been deactivated, it may be activated before RST expires.

Figure 16:
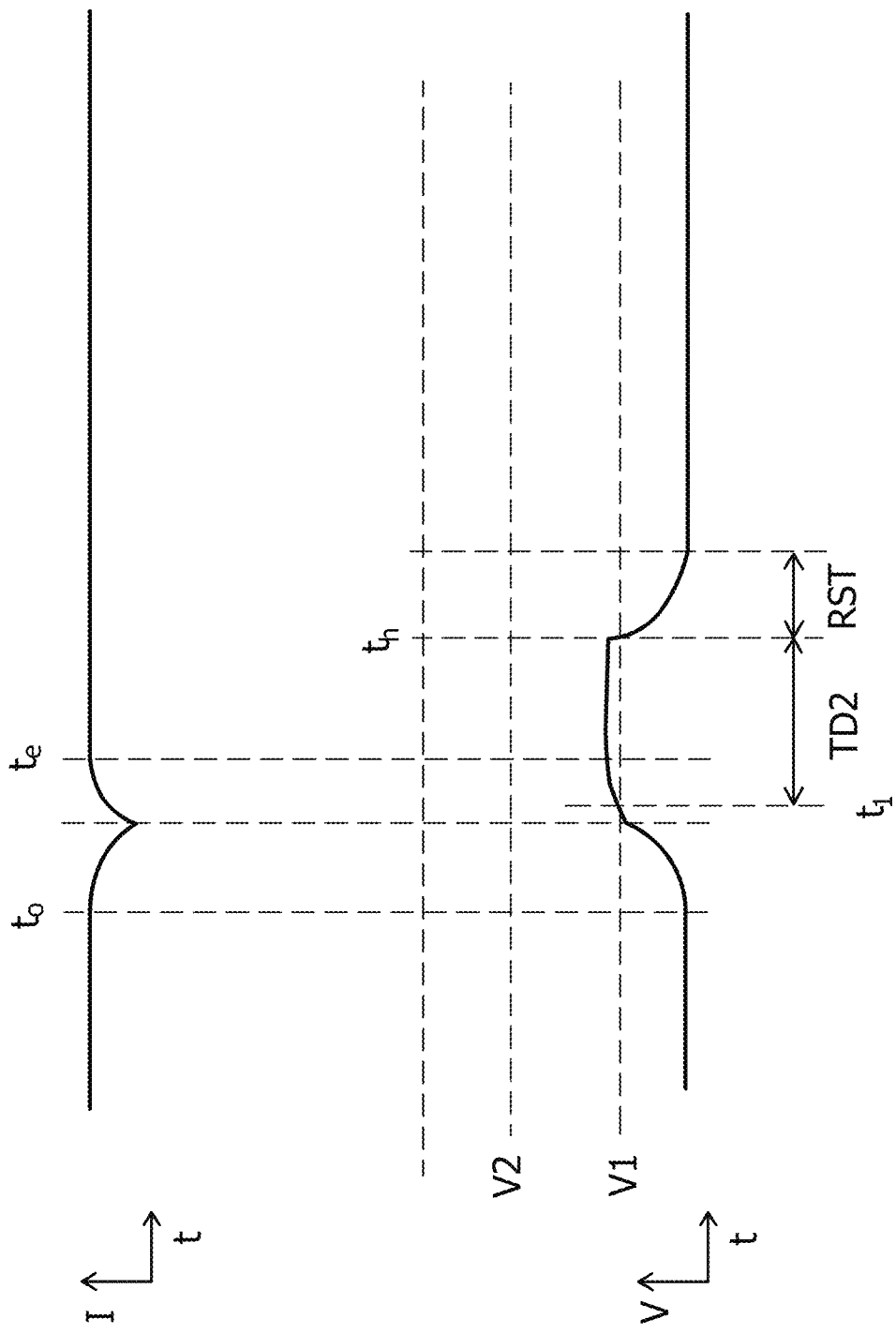
FIG. 16 schematically shows a temporal change of the electric current flowing through the electrode (upper curve) caused by noise (e.g., dark current), and a corresponding temporal change of the voltage of the electrode (lower curve), in the electronic system operating in the way shown in FIG. 15, according to an embodiment.

FIG. 16 schematically shows a temporal change of the electric current flowing through the electrode (upper curve) caused by noise (e.g., dark current, background radiation, scattered radiations, fluorescent radiations, shared charges from adjacent pixels), and a corresponding temporal change of the voltage of the electrode (lower curve), in the system 121 operating in the way shown in FIG. 15. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD2 and the controller 310 may deactivate the first voltage comparator 301 at the beginning of TD2. During TD2 (e.g., at expiration of TD2), the controller 310 activates the second voltage comparator 302. The noise is very unlikely large enough to cause the absolute value of the voltage to exceed the absolute value of V2 during TD2. Therefore, the controller 310 does not cause the number registered by the counter 320 to increase. At time $t_e$, the noise ends. At time $t_h$, the time delay TD2 expires. The controller 310 may be configured to deactivate the second voltage comparator 302 at expiration of TD2. After TD2 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 17:
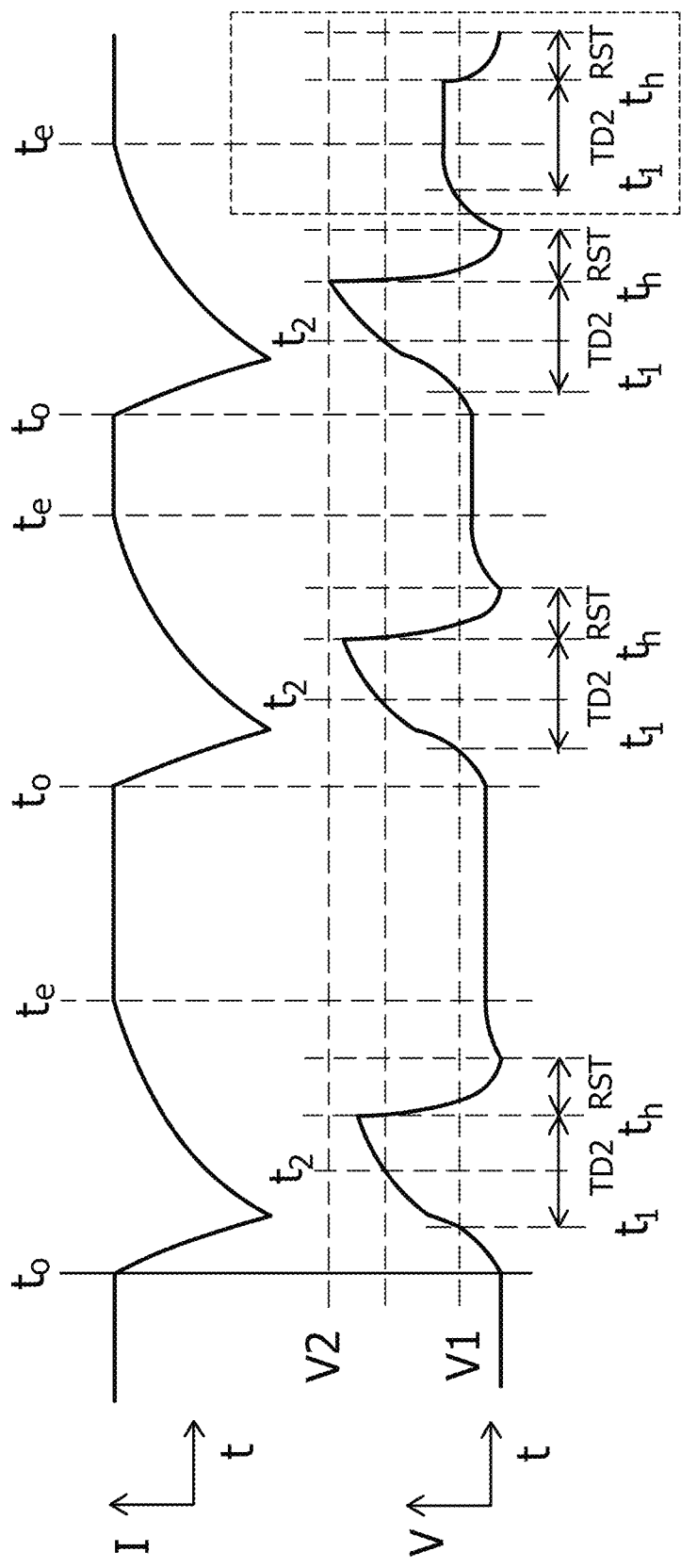
FIG. 17 schematically shows a temporal change of the electric current flowing through the electrode (upper curve) caused by charge carriers generated by a series of particles of radiation incident on the radiation absorption layer, and a corresponding temporal change of the voltage of the electrode, in the electronic system operating in the way shown in FIG. 15 with RST expires before $t_e$, according to an embodiment.

FIG. 17 schematically shows a temporal change of the electric current flowing through the electrode (upper curve) caused by charge carriers generated by a series of particles of radiation incident on the diode or the resistor, and a corresponding temporal change of the voltage of the electrode (lower curve), in the system 121 operating in the way shown in FIG. 15 with RST expires before $t_e$. The voltage curve caused by charge carriers generated by each incident particle of radiation is offset by the residue voltage before that particle. The absolute value of the residue voltage successively increases with each incident particle. When the absolute value of the residue voltage exceeds V1 (see the dotted rectangle in FIG. 17), the controller starts the time delay TD2 and the controller 310 may deactivate the first voltage comparator 301 at the beginning of TD2. If no other particle of radiation incidence on the diode or the resistor during TD2, the controller connects the electrode to the electrical ground during the reset time period RST at the end of TD2, thereby resetting the residue voltage. The residue voltage thus does not cause an increase of the number registered by the counter 320.

With reference to FIG. 1A and FIG. 1B, the first exposure of the object 50 to the first divergent radiation beam 11 for imaging as shown in FIG. 1A, and the second exposure of the object 50 to the second divergent radiation beam 13 for imaging as shown in FIG. 1B may be collectively referred to as the multiple exposure session of FIG. 1A and FIG. 1B. In general, a multiple exposure session may include N exposures, wherein N is an integer greater than 1. As an example, the multiple exposure session of FIG. 1A and FIG. 1B has N=2. As another example, the multiple exposure session of FIG. 8B has N=3 (corresponding to the 3 portion images 52A, 52B, and 52C).

In an embodiment, in the multiple exposure session of FIG. 1A and FIG. 1B, the image sensor 9000, the first radiation source 12, and the second radiation source 14 may rotate around the object 50 while the object 50 is stationary with respect to a system reference. In an embodiment, the system reference may be the earth. In an embodiment, the object 50 may be a plastic product. In an embodiment, the divergent radiation beams 11 and 13 may be X-rays with photon energy being less than 5 KeV.

Figure 18B:
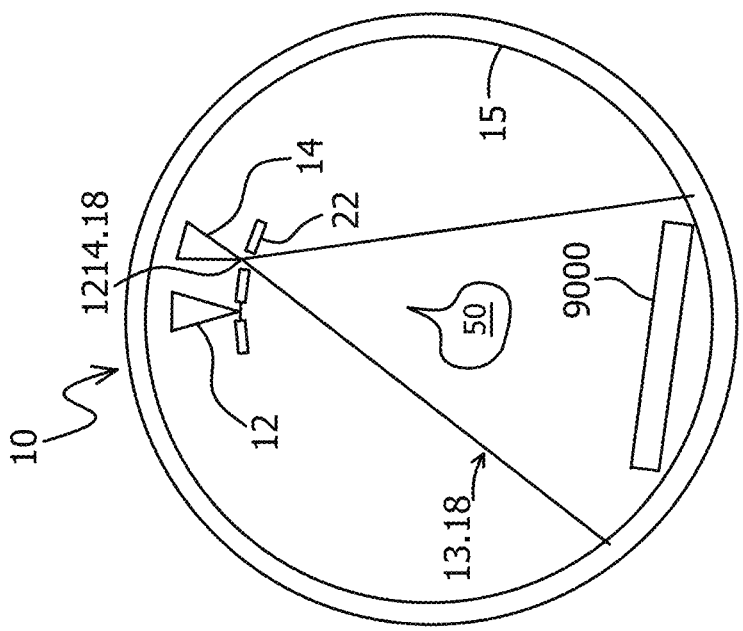
FIG. 18A and FIG. 18B show a multiple exposure session, according to an embodiment.
Figure 18A:
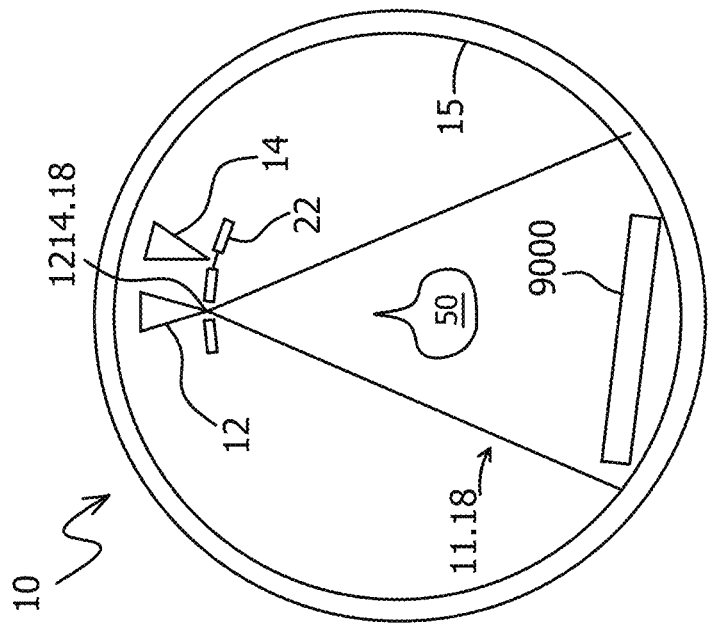

FIG. 18A and FIG. 18B show a multiple exposure session, according to an embodiment. In an embodiment, the multiple exposure session of FIG. 18A and FIG. 18B may be similar to the multiple exposure session of FIG. 1A and FIG. 1B, except that in the multiple exposure session of FIG. 18A and FIG. 18B, the object 50 may rotate (e.g., clockwise as shown) with respect to the image sensor 9000, the first radiation source 12, and the second radiation source 14 while the image sensor 9000, the first radiation source 12, and the second radiation source 14 are stationary with respect to the system reference.

In an embodiment, the rotation of the object 50 may be around a rotation axis perpendicular to an apparatus plane which intersects the image sensor 9000, the first radiation source 12, and the second radiation source 14. For example, in FIG. 18A and FIG. 18B, if the apparatus plane is on or parallel to the drawing page, then the rotation axis of the object 50 is perpendicular to the drawing page.

In an embodiment, the rotation axis of the object 50 is on a straight line going through the center of the earth. In other words, the apparatus plane which is perpendicular to the rotation axis is parallel to an area of the earth surface closest to the apparatus 10.

Figure 19:
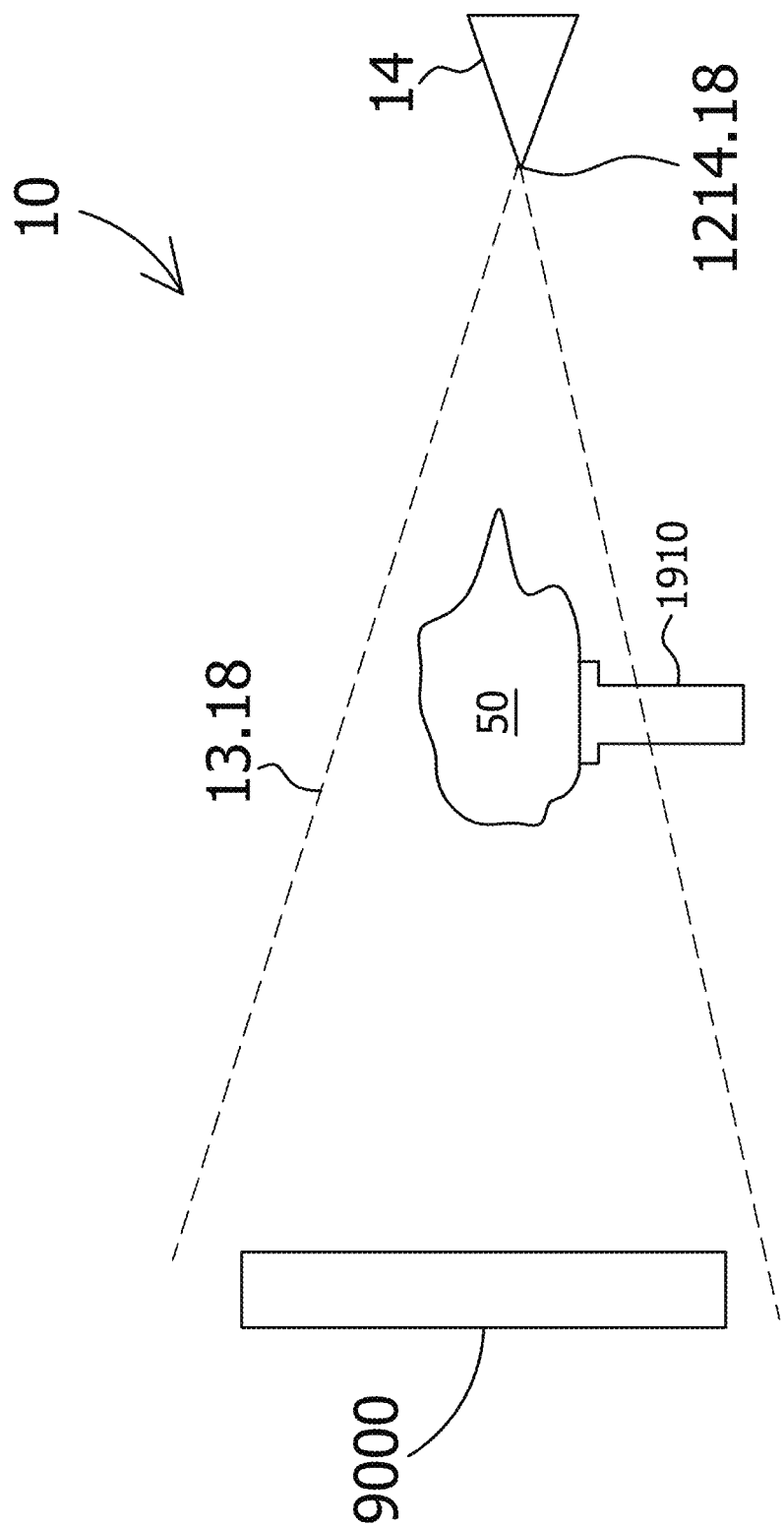
FIG. 19 schematically shows a simplified side view of the apparatus of FIG. 18B, according an embodiment.

FIG. 19 schematically shows a simplified side view of the apparatus 10 of FIG. 18B, according an embodiment. Specifically, the apparatus 10 may further comprise a platform 1910. In an embodiment, the object 50 may be physically fixed to the platform 1910. In other words, the relative positions between the object 50 and the platform 1910 are fixed. For example, the object 50 may be strapped to, tied to, or just placed on the platform 1910. In an embodiment, the platform 1910 may be configured to rotate with respect to the image sensor 9000, the first radiation source 12, and the second radiation source 14 thereby causing the object 50 to rotate with respect to the image sensor 9000, the first radiation source 12, and the second radiation source 14.

Figure 20:
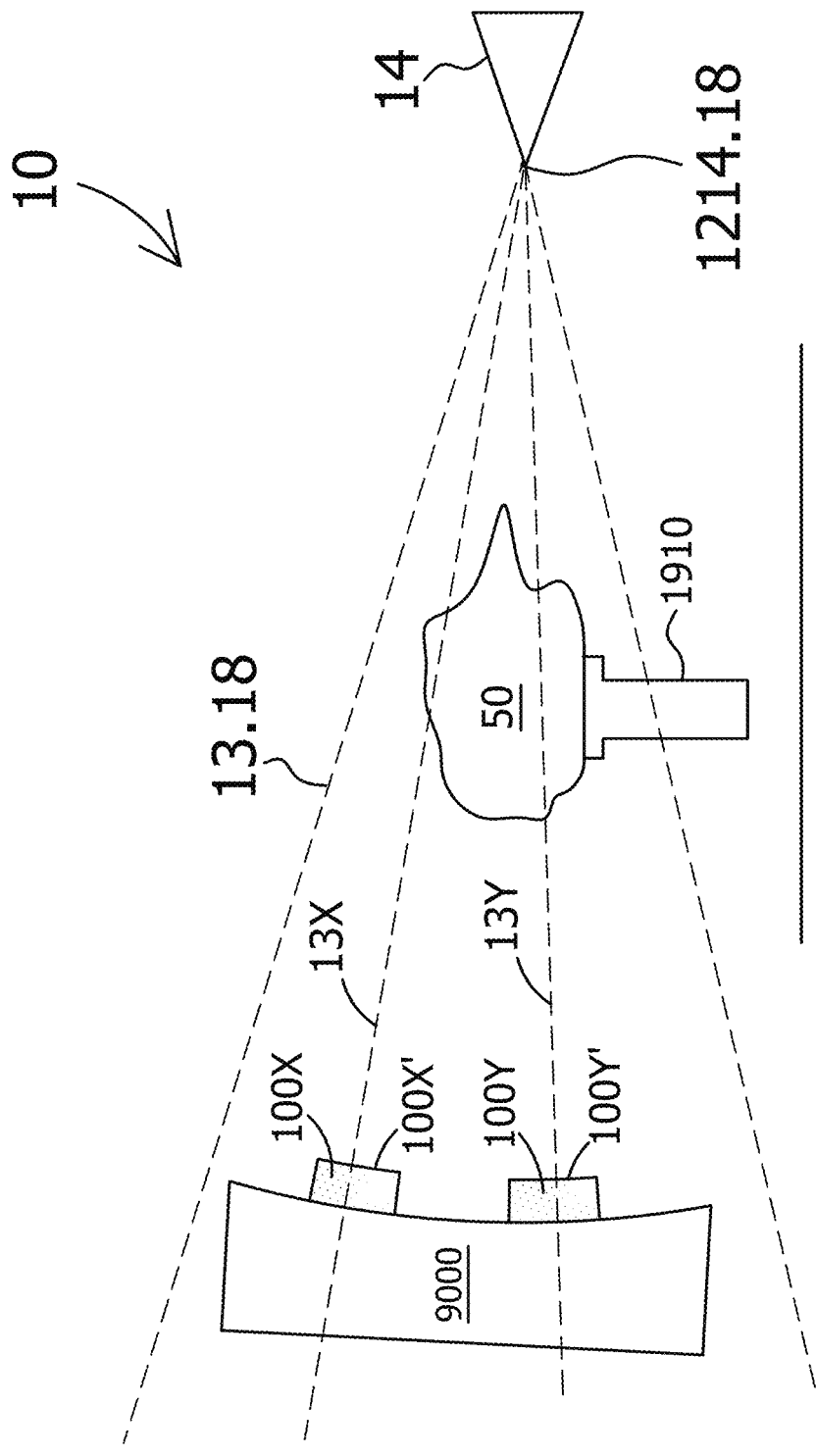
FIG. 20 schematically shows the image sensor of FIG. 19 in more detail, according to an embodiment.

FIG. 20 schematically shows the image sensor 9000 of FIG. 19 in more detail, according to an embodiment. Specifically, in an embodiment, the radiation detectors 100 (e.g., radiation detectors 100X and 100Y) of the image sensor 9000 may be arranged on the image sensor 9000 such that their respective radiation receiving surfaces (e.g., radiation receiving surfaces 100X' and 100Y') are not all parallel to each other. The radiation receiving surface of a radiation detector 100 is a surface of the radiation detector 100 that is (A) parallel to a pixel plane which intersects all the pixels (i.e., sensing elements) 150 of the radiation detector 100 and (B) closest to the pixel plane.

In an embodiment, for each radiation detector 100 of the image sensor 9000, any straight line going through said radiation detector 100 and either the first radiation source 12 or the second radiation source 14 is essentially perpendicular (i.e., perpendicular or almost perpendicular) to the radiation receiving surface of said radiation detector 100. As a result, any radiation particle propagating from any radiation source (12 or 14) toward any radiation detector 100 of the image sensor 9000 follows a path essentially perpendicular to the receiving surface of the radiation detector 100.

For example, with reference to FIG. 20, the straight line 13X going through the radiation detector 100X and the second radiation source 14 is essentially perpendicular to the radiation receiving surface 100X' of the radiation detector 100X. Similarly, the straight line 13Y going through the radiation detector 100Y and the second radiation source 14 is essentially perpendicular to the radiation receiving surface 100Y' of the radiation detector 100Y.

Figure 21B:
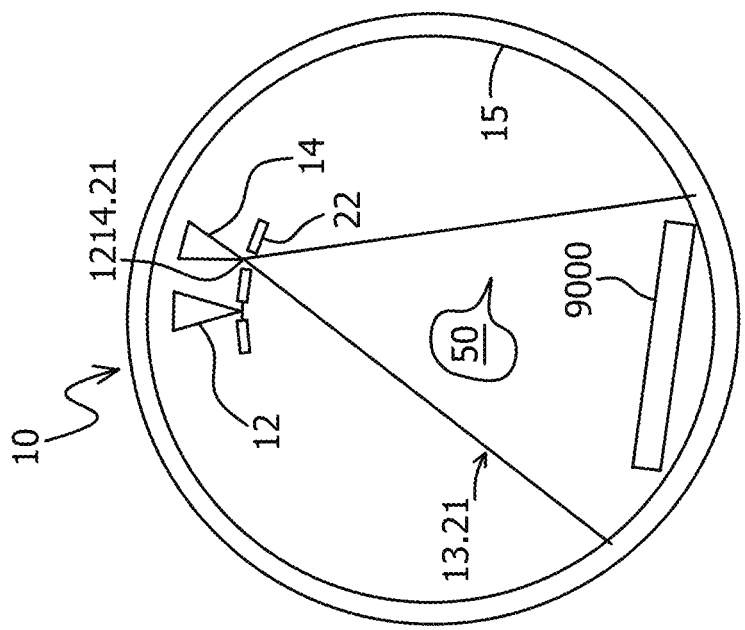
FIG. 21A and FIG. 21B schematically show another multiple exposure session, according to an embodiment.
Figure 21A:
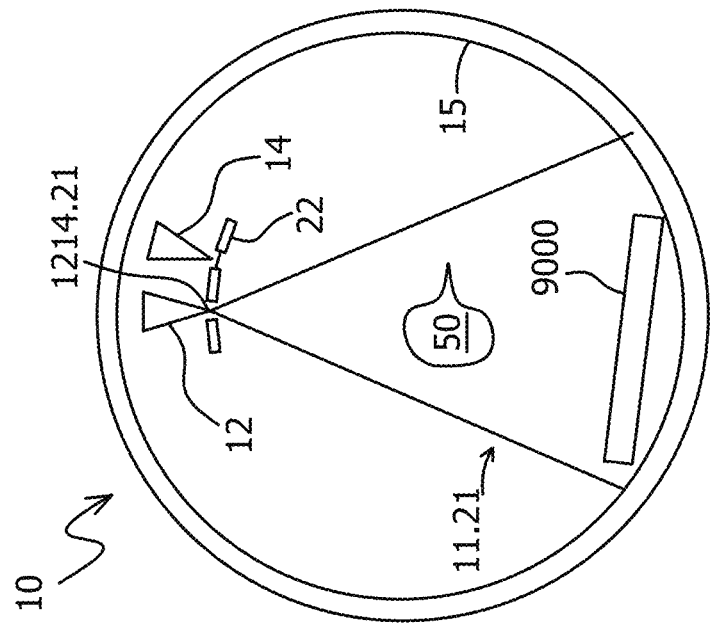

FIG. 21A and FIG. 21B schematically show another multiple exposure session, according to an embodiment. In an embodiment, the multiple exposure session of FIG. 21A and FIG. 21B may be similar to the multiple exposure session of FIG. 18A and FIG. 18B, except for a different relative radiating position 1214.21 with respect to the object 50. More specifically, in an embodiment, after the second exposure (FIG. 18B) of the multiple exposure session of FIG. 18A and FIG. 18B, the object 50 may rotate clockwise to a position as shown in FIG. 21A. Then, the first exposure of the multiple exposure session of FIG. 21A and FIG. 21B may be performed as shown in FIG. 21A (i.e., with divergent radiation beam 11.21 emitted by the radiation source 12 from the relative radiating position 1214.21 with respect to the object 50). After that, in an embodiment, the object 50 may further rotate clockwise to a position as shown in FIG. 21B. Then, the second exposure of the multiple exposure session of FIG. 21A and FIG. 21B may be performed as shown in FIG. 21B (i.e., with divergent radiation beam 13.21 emitted by the radiation source 14 also from the relative radiating position 1214.21 with respect to the object 50).

As a result of the first and second exposures of the multiple exposure session of FIG. 21A and FIG. 21B, two portion images of different portions of the object 50 may be captured. Next, in an embodiment, a stitched image of the object 50 may be formed by stitching these 2 portion images. In general, M multiple exposure sessions (similar to the multiple exposure session of FIG. 18A and FIG. 18B and the multiple exposure session of FIG. 21A and FIG. 21B) with M different relative radiating positions with respect to the object 50 may be performed one by one resulting in M stitched images of the object 50 (M is an integer greater than 1).

Next, in an embodiment, a 3D (three dimensional) image of the object surface of the object 50 may be formed based on the M stitched images. Next, in an embodiment, a mold (not shown) may be formed based on and conforming to the 3D image of the object surface of the object 50. Next, in an embodiment, copies of the object 50 may be produced using the mold.

FIG. 22 shows a flowchart 2200 summarizing and generalizing an operation of the apparatus 10, according to an embodiment. In step 2210, components of the apparatus 10 and the object 50 may be positioned for imaging. Specifically, for i=1, . . . ,M, and j=1, . . . ,N, a radiation source (j) and the object 50 are positioned such that the radiation source (j) is at a same relative radiating position (i) with respect to the object 50. For example, for i=j=1 (FIG. 18A), the radiation source (1) (i.e., radiation source 12) is at the same relative radiating position (1) (i.e., relative radiating position 1214.18) with respect to the object 50. For another example, for i=1 and j=2 (FIG. 18B), the radiation source (2) (i.e., radiation source 14) is at the same relative radiating position (1) (i.e., relative radiating position 1214.18) with respect to the object 50.

In step 2220, divergent radiation beams are directed toward the object 50. Specifically, a divergent radiation beam (i,j) is directed from the radiation source (j) toward the object 50 while the radiation source (j) is at the relative radiating position (i) with respect to the object 50.

For example, for i=j=1 (FIG. 18A), the divergent radiation beam (1,1) (i.e., divergent radiation beam 11.18) is directed from the radiation source (1) (i.e., radiation source 12) toward the object 50 while the radiation source (1) is at the relative radiating position (1) (i.e., relative radiating position 1214.18) with respect to the object 50. For another example, for i=1 and j=2 (FIG. 18B), the divergent radiation beam (1,2) (i.e., divergent radiation beam 13.18) is directed from the radiation source (2) (i.e., radiation source 14) toward the object 50 while the radiation source (2) is at the relative radiating position (1) (i.e., relative radiating position 1214.18) with respect to the object 50.

In step 2230, portion images of portions of the object 50 may be captured. Specifically, a portion image (i,j) of a portion of the object 50 may be captured using the image sensor 9000 with the divergent radiation beam (i,j).

For example, for i=j=1 (FIG. 18A), a portion image (1,1) of a portion of the object 50 may be captured using the image sensor 9000 with the divergent radiation beam (1,1) (i.e., divergent radiation beam 11.18). For another example, for i=1 and j=2 (FIG. 18B), a portion image (1,2) of a portion of the object 50 may be captured using the image sensor 9000 with the divergent radiation beam (1,2) (i.e., divergent radiation beam 13.18).

In step 2240, stitched images may be formed. More specifically, for i=1, . . . ,M, a stitched image (i) of the object 50 may be formed by stitching the portion images (i,j), j=1, . . . ,N.

For example, for i=1 (FIG. 18A and FIG. 18B), a stitched image (1) of the object 50 may be formed by stitching the portion image (1,1) (FIG. 18A) and the portion image (1,2) (FIG. 18B). For another example, for i=2 (FIG. 21A and FIG. 21B), a stitched image (2) of the object 50 may be formed by stitching the portion image (2,1) (FIG. 21A) and the portion image (2,2) (FIG. 21B).

Next, in an embodiment, a 3D image of the object surface of the object 50 may be formed based on the M stitched images of the object 50. Then, in an embodiment, a mold may be formed based on and conforming to the 3D image of the object surface of the object 50. Then, in an embodiment, copies of the object 50 may be produced using the mold.

In the embodiments described above and related to FIG. 18A, FIG. 18B, FIG. 21A, and FIG. 21B, the chronological order of the exposures of the multiple exposure sessions is as follows: the exposure as shown FIG. 18A (or just FIG. 18A for short), then FIG. 18B, then FIG. 21A, and then FIG. 21B. In general, the chronological order of the exposures of the multiple exposure sessions may be arbitrary. For example, the chronological order of the exposures may be FIG. 18B, then FIG. 18A, then FIG. 21A, and then FIG. 21B. For another example, the chronological order of the exposures may even be FIG. 18A, then FIG. 21B, then FIG. 18B, and then FIG. 21A.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
   a first radiation source configured to produce a first divergent radiation beam toward an object;
   a second radiation source configured to produce a second divergent radiation beam toward the object; and
   an image sensor;
   wherein the object is configured to rotate with respect to the image sensor, the first radiation source, and the second radiation source,
   wherein relative positions among the image sensor, the first radiation source, and the second radiation source are fixed;
   wherein the image sensor comprises a plurality of radiation detectors spaced apart from one another;
   wherein the image sensor is configured to capture, by using the radiation detectors and with the first divergent radiation beam, an image of a first portion of the object, and is configured to capture, by using the radiation detectors and with the second divergent radiation beam, an image of a second portion of the object; and
   wherein the image sensor is configured to form an image of the object by stitching the image of the first portion and the image of the second portion.

2. The apparatus of claim 1, wherein the image sensor, the first radiation source, and the second radiation source are stationary.

3. The apparatus of claim 1, wherein the first and second divergent radiation beams are X-rays with photon energy being less than 5 KeV.

4. The apparatus of claim 1, wherein said rotation of the object is around a rotation axis perpendicular to an apparatus plane which intersects the image sensor, the first radiation source, and the second radiation source.

5. The apparatus of claim 1, further comprising a platform,
wherein the object is physically fixed to the platform, and
wherein the platform is configured to rotate with respect to the image sensor, the first radiation source, and the second radiation source.

6. The apparatus of claim 1, further comprising a controller configured to activate and deactivate the first radiation source independently from the second radiation source, and configured to activate and deactivate the second radiation source independently from the first radiation source.

7. The apparatus of claim 1, wherein the image sensor is configured to capture an image of a portion of the object with the first divergent radiation beam or with the second divergent radiation beam.

8. The apparatus of claim 1,
wherein the image sensor comprises a collimator with a plurality of radiation transmitting zones and a radiation blocking zone;
wherein the radiation blocking zone is configured to block radiation that would otherwise incident on a dead zone of the image sensor, and the radiation transmitting zones are configured to transmit at least a portion of radiation that would incident on active areas of the image sensor.

9. The apparatus of claim 1, further comprising a mask with a plurality of radiation transmitting zones and a radiation blocking zone;
wherein the radiation blocking zone is configured to block a portion of the first divergent radiation beam that would otherwise incident on a dead zone of the image sensor through the object, and the radiation transmitting zones are configured to transmit at least a portion of the first divergent radiation beam that would incident on active areas of the image sensor.

10. The apparatus of claim 1, wherein the radiation detectors respectively comprise radiation receiving surfaces not all parallel to each other.

11. The apparatus of claim 1, wherein for each radiation detector of the radiation detectors, any straight line going through said radiation detector and either the first radiation source or the second radiation source is essentially perpendicular to a radiation receiving surface of said radiation detector.

12. The apparatus of claim 1, wherein the first radiation source is at a first radiating position relative to the object when the image sensor captures the image of the first portion of the object and the second radiation source is at a second radiating position relative to the object when the image sensor captures the image of the second portion of the object; wherein the first radiating position and the second radiating position are the same.

13. The apparatus of claim 1, wherein at least some of the plurality of radiation detectors are arranged in staggered rows.

14. The image sensor of claim 1, wherein radiation detectors in a same row are uniform in size; wherein a distance between two neighboring radiation detectors in a same row is greater than a width of one radiation detector in the same row in an extending direction of the row and is less than twice that width.

15. The apparatus of claim 1, wherein at least some of the plurality of radiation detectors are rectangular in shape.

16. The apparatus of claim 1, wherein at least some of the plurality of radiation detectors are hexagonal in shape.

17. The apparatus of claim 1, wherein at least one of the plurality of radiation detectors comprises a radiation absorption layer and an electronics layer;
wherein the radiation absorption layer comprises an electrode;
wherein the electronics layer comprises an electronic system;
wherein the electronic system comprises:
a first voltage comparator configured to compare a voltage of the electrode to a first threshold,
a second voltage comparator configured to compare the voltage to a second threshold,
a counter configured to register a number of particles of radiation reaching the radiation absorption layer, and
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, if the second voltage comparator determines that an absolute value of the voltage equals or exceeds an absolute value of the second threshold.

18. The apparatus of claim 17, wherein the electronic system further comprises an integrator electrically connected to the electrode, wherein the integrator is configured to collect charge carriers from the electrode.

19. The apparatus of claim 17, wherein the controller is configured to activate the second voltage comparator at a beginning or expiration of the time delay.

20. The apparatus of claim 17, wherein the electronic system further comprises a voltmeter, wherein the controller is configured to cause the voltmeter to measure the voltage upon expiration of the time delay.

21. The apparatus of claim 17, wherein the controller is configured to determine an energy of particles of radiation based on a value of the voltage measured upon expiration of the time delay.

22. The apparatus of claim 17, wherein the controller is configured to connect the electrode to an electrical ground.

23. The apparatus of claim 17, wherein a rate of change of the voltage is substantially zero at expiration of the time delay.

24. The apparatus of claim 17, wherein a rate of change of the voltage is substantially non-zero at expiration of the time delay.

25. An apparatus comprising:
a first radiation source configured to produce a first divergent radiation beam toward an object;
a second radiation source configured to produce a second divergent radiation beam toward the object; and
an image sensor;
a shutter configured to controllably block the first divergent radiation beam from reaching the object, and to controllably block the second divergent radiation beam from reaching the object;

wherein the object is configured to rotate with respect to the image sensor, the first radiation source, and the second radiation source, wherein relative positions among the image sensor, the first radiation source, and the second radiation source are fixed.

26. A method, comprising:

for i=1, . . . ,M, and j=1, . . . ,N, positioning a radiation source (j) and a same object such that the radiation source (j) is at a same relative radiating position (i) with respect to the object;

directing a divergent radiation beam (i,j) from the radiation source (j) toward the object while the radiation source (j) is at the relative radiating position (i) with respect to the object;

capturing a portion image (i,j) of a portion of the object using a same image sensor with the divergent radiation beam (i,j); and for i=1, . . . ,M, forming a stitched image (i) of the object by stitching the portion images (i,j), j=1, . . . ,N, wherein said positioning comprises rotating the object with respect to the image sensor and the radiation sources (j), j=1, . . . ,N, wherein relative positions among the image sensor and the radiation sources (j), j=1, . . . , N are fixed, and wherein M and N are integers greater than 1.

27. The method of claim 26, wherein the image sensor and the radiation sources (j), j=1, . . . ,N are stationary.

28. The method of claim 26, wherein the divergent radiation beam (i,j) is X-ray with photon energy being less than 5 KeV.

29. The method of claim 26, wherein said rotation of the object is around a rotation axis perpendicular to an apparatus plane which intersects the image sensor and the radiation sources (j), j=1, . . . ,N.

30. The method of claim 26, wherein the object is physically fixed to a platform, and wherein said rotating the object comprises rotating the platform.

31. The method of claim 26, wherein:

each radiation source of the radiation sources (j), j=1, . . . ,N is deactivated while said radiation source is not at a relative radiating position of the relative radiating positions (i), i=1, . . . ,M.

32. The method of claim 26, wherein:

radiation produced by each radiation source of the radiation sources (j), j=1, . . . ,N is blocked while said radiation source is not at a relative radiating position of the relative radiating positions (i), i=1, . . . ,M.

33. The method of claim 26, wherein a portion of each divergent radiation beam of the divergent radiation beams (i,j), i=1, . . . ,M, and j=1, . . . ,N that would otherwise incident on a dead zone of the image sensor through the object is blocked.

34. The method of claim 26, wherein the image sensor comprises a plurality of radiation detectors spaced apart from one another, and wherein said capturing the portion image (i,j) of a portion of the object comprises receiving a portion of the divergent radiation beam (i,j) that has transmitted through the object, with the radiation detectors.

35. The method of claim 34, wherein the radiation detectors respectively comprise radiation receiving surfaces not all parallel to each other.

36. The method of claim 34, wherein for each radiation detector of the radiation detectors, any straight line going through said radiation detector and any radiation source of the radiation sources (j), j=1, . . . ,N is essentially perpendicular to a radiation receiving surface of said radiation detector.

37. The method of claim 26, wherein for i=1, . . . ,M, the portion images (i,j), j=1, . . . ,N have spatial overlaps.

38. The method of claim 26, further comprising forming a 3D (three dimensional) image of an object surface of the object based on the stitched images (i), i=1, . . . , M.

39. The method of claim 38, further comprising forming a mold based on and conforming to the 3D image of the object surface.

* * * * *